(12) United States Patent
Chiarello et al.

(10) Patent No.: US 7,932,393 B2
(45) Date of Patent: Apr. 26, 2011

(54) INSECTICIDAL (HETEROARYLALKY)ALKANE THIO AND OXO AMINE DERIVATIVES

(75) Inventors: John F. Chiarello, Newton, PA (US); Harvey R. Wendt, Medford Lakes, NJ (US); Nanjing Zhang, Princeton, NJ (US); George Theodoridis, Princeton, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 12/223,279

(22) PCT Filed: Jan. 15, 2007

(86) PCT No.: PCT/EP2007/000288
§ 371 (c)(1),
(2), (4) Date: Jun. 8, 2010

(87) PCT Pub. No.: WO2007/085356
PCT Pub. Date: Aug. 2, 2007

(65) Prior Publication Data
US 2010/0261757 A1 Oct. 14, 2010

Related U.S. Application Data

(60) Provisional application No. 60/763,072, filed on Jan. 27, 2006.

(51) Int. Cl.
*C07D 213/04* (2006.01)
(52) U.S. Cl. ..................................................... 546/255
(58) Field of Classification Search ................... None
See application file for complete search history.

*Primary Examiner* — Janet L Andres
*Assistant Examiner* — Heidi Reese

(57) ABSTRACT

Certain novel N-(heteroarylalkyl)alkanediamine derivatives have provided unexpected insecticidal and acaricidal activity. These compounds are represented by formula I: wherein Ar, a, b, c, T, W, Y, R, $R^f$, $R^g$, $R^h$, $R^i$, $R^j$, $R^k$, $R^m$, $R^n$, and $R^7$ are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

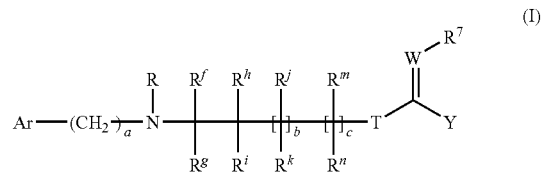

7 Claims, 1 Drawing Sheet

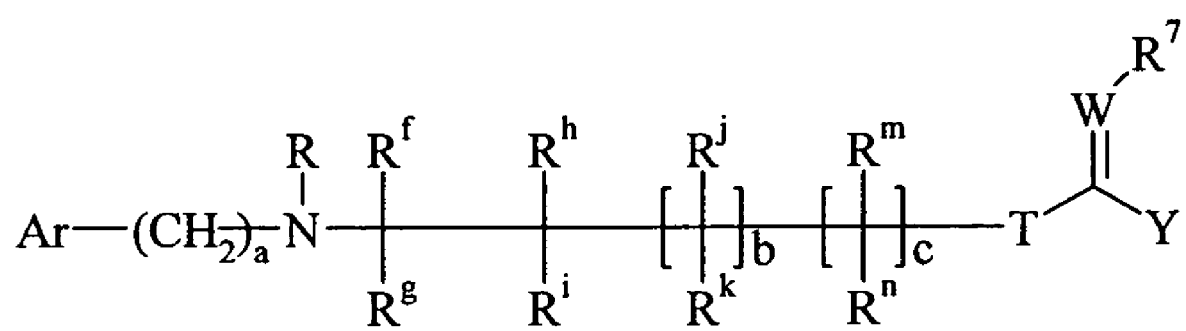
I

INSECTICIDAL (HETEROARYLALKY)ALKANE THIO AND OXO AMINE DERIVATIVES

FIELD OF THE INVENTION

The present invention generally relates to pesticidal compounds and their use in controlling insects and acarids. In particular, it pertains to compositions of pesticidal (heteroarylalkyl)alkane thio and oxo amine derivatives and agriculturally acceptable salts thereof, and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Although there are many orders of insects that can cause significant crop damage, insects, for example, of the order "*Homoptera*" are of major importance. The suborder *Homoptera* includes, for example, aphids, leafhoppers, cicadas, whiteflies, and mealybugs, to name a few. *Homoptera* have piercing/sucking mouthparts, enabling them to feed by withdrawing sap from vascular plants. Insect damage from *homoptera* is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some *homoptera* have toxic saliva that is injected into plants while they are feeding. The saliva can cause plant damage through disfigurement and in some instances plant death. *Homoptera* can also vector disease-causing pathogens. Unlike direct damage, it does not take a large number of disease-vectoring insects to cause considerable damage to crop plants.

Thus, there is a continuing demand for new insecticides, and for new acaricides that are safer, more effective, and less costly. Insecticides and acaricides are useful for controlling insects and acarids which may otherwise cause significant damage both above and below the soil level to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents disclose some alkanediamine compounds that are reported to be insecticidally active. For example, U.S. Pat. No. 4,806,553 discloses certain insecticidal alkylenediamine compounds of the general formula I:

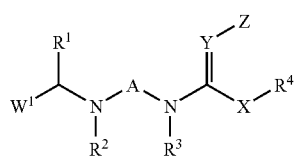

where $W^1$ is a five- or six-membered heterocyclic group, which may be substituted, containing at least one heteroatom selected from —O—, —S—, and —N—;

$R^1$, $R^2$, and $R^3$ are hydrogen or alkyl;

$R^4$ is hydrogen, alkyl, aryl, aralkyl, alkoxy, dialkylamino, alkoxyalkyl, alkylthioalkyl, or —CH$_2$—W$^2$— in which $W^2$ has the same meaning as $W^1$;

X is —S—, —NR$^5$—, or a single bond, in which R$^5$ is hydrogen or alkyl, and in the case where X is —NR$^5$—, the group —NR$^4$R$^5$—, in the formula I may have the same meaning as the group

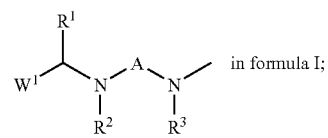

Y is —N—, or =CR$^6$—, in which R$^6$ is hydrogen, alkyl, aryl, acyl, alkoxycarbonyl, or cyano;

Z is cyano or nitro; and,

A is ethylene or trimethylene, which may be substituted with alkyl.

Published Japanese Patent Application 08269035A discloses certain tetrahydrofuran-3-ylmethyl derivatives of the general formula I:

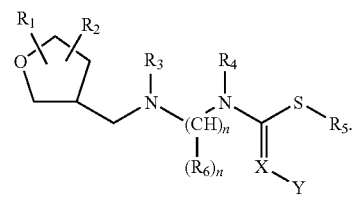

where $R_1$ and $R_2$ are hydrogen, or optionally substituted $C_1$-$C_5$-alkyl; $R_3$-$R_5$ are hydrogen, optionally substituted $C_1$-$C_5$-alkyl, optionally substituted $C_2$-$C_5$-alkenyl, or optionally substituted $C_2$-$C_5$-alkynyl; n is 2-5; $R_6$ is hydrogen or $C_1$-$C_3$-alkyl; X is CH or N; Y is NO$_2$ or C≡N; a $R_3$ and $R_4$ together may form a ring.

U.S. Pat. No. 3,929,857 claims compounds of the following general formula that are useful as accelerators for the vulcanization of rubber:

(CN)$_2$C=C(S-A-NRR$_1$)$_2$ where

A is alkylene of 2-4 carbon atoms, and R and R$_1$ independently are lower alkyl, araalkyl of 7-10 carbon atoms, cycloalkyl of 5-8 carbon atoms or R and R$_1$ together with the nitrogen is a heterocyclic radical of 4-8 carbon atoms.

U.S. Pat. No. 5,883,134 discloses a method of controlling microorganisms using compounds of the following general formula:

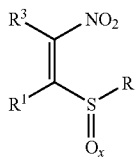

where $R^1$ is selected from $R^2SO_y$, H, and $(C_1-C_{18})$alkyl;

R and $R^2$ are independently selected from $(C_1-C_{18})$alkyl;

R and $R^2$ can be joined, together with the atoms to which they are attached, to form a 5-membered or 6-membered saturated or unsaturated ring, said ring optionally fused to a substituted or unsubstituted phenyl ring;

R and $R^1$ can be joined, together with the atoms to which they are attached, to form a 5-membered or 6-membered saturated or unsaturated ring;

$R^3$ is selected from H, and $(C_1-C_6)$alkyl;

$R^1$ and $R^3$ or R and $R^3$ can be joined, together with the atoms to which they are attached, to form a 5-membered or 6-membered unsaturated ring;

x=1 or 2; and y=0, 1, or 2.

There is no disclosure or suggestion in any of the above-referenced patents or patent application of the structures and insecticidal and acaricidal activity of the compounds of the present invention.

SUMMARY OF THE INVENTION

In accordance with the present invention, it has now been found that certain novel (heteroarylalkyl)alkane thio and oxo amine derivatives are surprisingly active in the control of insects and acarids when used in the insecticidal and acaricidal compositions and methods of this invention. The compounds of formula I are represented by the following general formula:

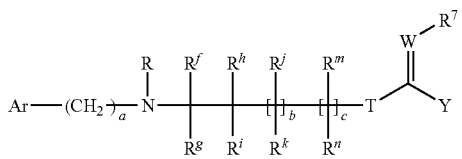

I where

Ar is selected from

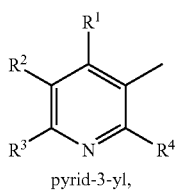

(A)

pyrid-3-yl,

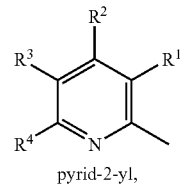

(A1)

pyrid-2-yl,

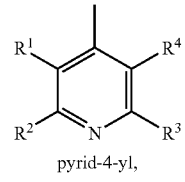

(A2)

pyrid-4-yl,

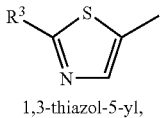

(B)

1,3-thiazol-5-yl,

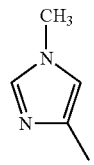

(C)

1-methyl-imidazol-4-yl,

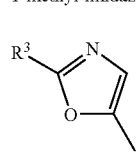

(D)

1,3-oxazol-5-yl,

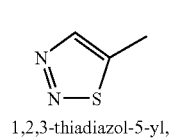

(E)

1,2,3-thiadiazol-5-yl,

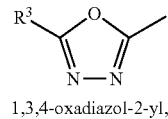

(F)

1,3,4-oxadiazol-2-yl,

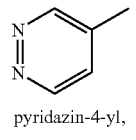

(G)

pyridazin-4-yl,

(H)

pyrimidin-5-yl,

(J)

pyridazin-3-yl,

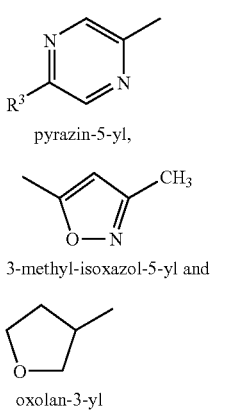

pyrazin-5-yl, 3-methyl-isoxazol-5-yl and oxolan-3-yl where

R¹, R², R³, and R⁴ are independently selected from hydrogen, halogen, alkyl, alkoxy, haloalkyl, and haloalkoxy;

and, a is an integer selected from 0 or 1;

R is selected from hydroxy, alkyl, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-R⁸-1,3-thiazol-4-ylmethyl, 5-R⁸-1,2,4-oxadiazol-3-ylmethyl,

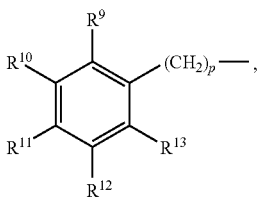 (1)

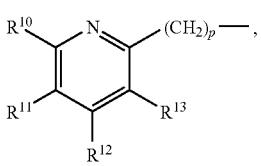 (2)

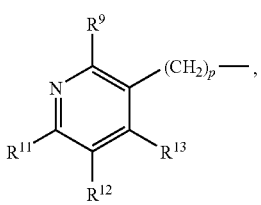 (3)

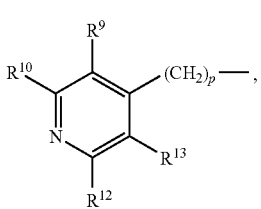 (4)

$$—(CH_2)_p—CR^{14}=CR^{15}R^{16} \text{ and} \quad (5)$$

$$—(CH_2)_p—C\equiv CR^{17}, \quad (6)$$

where

R⁸ is selected from halogen, alkyl, aryl, and heteroaryl, wherein aryl and heteroaryl are optionally substituted with at least one of halogen, alkyl, haloalkyl, alkoxy, and haloalkoxy;

p is an integer selected from 1 or 2;

and,

R⁹, R¹⁰, R¹¹, R¹², and R¹³ are independently selected from hydrogen, halogen, alkyl, haloalkyl, alkoxy, haloalkoxy, alkoxyimino, dialkylaminoalkyl, cyano, nitro, 2-alkyl-2H-tetrazol-5-yl, aryl, and aryloxy;

R¹⁴, R¹⁵ and R¹⁶ are independently selected from hydrogen, halogen, alkyl and aryl;

R¹⁷ is selected from hydrogen, alkyl,

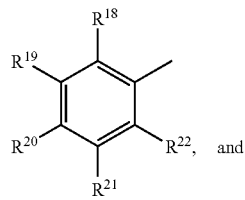 (7)

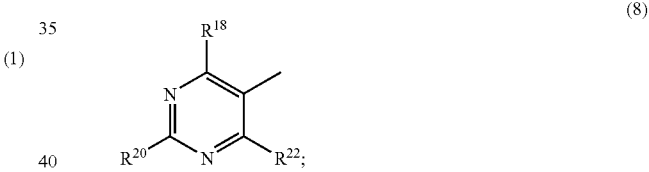 (8)

where

R¹⁸, R¹⁹, R²⁰, R²¹, and R²² are independently selected from hydrogen, halogen, alkyl, haloalkyl, alkoxy, and haloalkoxy;

b and c are integers independently selected from 0 or 1;

$R^f$, $R^g$, $R^h$, $R^i$, $R^j$, $R^k$, $R^m$ and $R^n$ are independently selected from hydrogen and alkyl;

T is selected from —O—, —S—, —CR³⁴R³⁵—;

Y is selected from —X—R⁶ and;

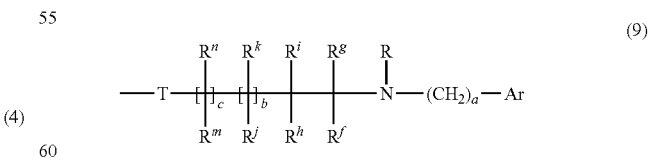 (9)

where

X is selected from —O—, —S—, and —CR³⁴R³⁵—;

R⁶ is selected from hydrogen, alkyl, cycloalkyl, cycloalkylalkyl, alkoxy, alkoxyalkyl, alkoxyalkoxyalkyl, alkenyl, haloalkenyl, alkynyl and

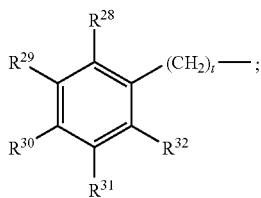

where t is an integer selected from 0, 1 and 2;
and,
$R^{28}$, $R^{29}$, $R^{30}$, $R^{31}$ and $R^{32}$ are independently selected from hydrogen, halogen, alkyl, haloalkyl, alkoxy, and haloalkoxy;
Ar, R, $R^f$, $R^g$, $R^h$, $R^i$, $R^j$, $R^k$, $R^m$, $R^n$, a, b and c have the same meaning as stated above;
$R^7$ is selected from —C≡N and —NO$_2$;
W is selected from —CR$^{33}$— and —N—;
$R^{33}$, $R^{34}$, and $R^{35}$ are independently selected from hydrogen and alkyl;
where
provided that when I) i) Ar is pyrid-3-yl (A); ii) a is 1 and b and c are 0 and $R^f$ through $R^i$, inclusively, are hydrogen; iii) R is cycloalkylalkyl; iv) T is —S—; v) $R^7$ is —C≡N; and v) Y is

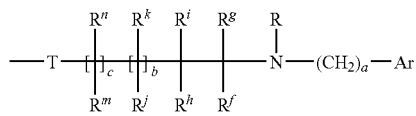

where Ar, R, $R^f$, $R^g$, $R^h$, $R^i$, a, b and c have the same meaning as stated above; vi) then W is —N—;

II) i) a is 1 and b and c are 0, and $R^f$ through $R^i$, inclusively, are hydrogen; ii) R is cyanoalkyl; iii) T is —S—; iv) W is —N—; v) $R^7$ is —C≡N; and vi) Y is

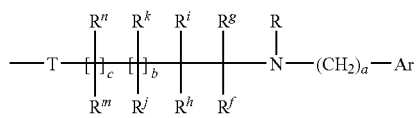

where Ar, R, $R^f$, $R^g$, $R^h$, $R^i$, a, b and c have the same meaning as stated above; vii) then Ar is other than 2-chloro-1,3-thiazol-5-yl;

the N-oxides thereof; and
agriculturally acceptable salts thereof.

The present invention is also directed to compositions containing an insecticidally effective amount of at least one of a compound of formula I, and optionally, an effective amount of at least one of a second compound, with at least one insecticidally compatible carrier.

The present invention is also directed to methods of controlling insects, where control is desired, which comprise applying an insecticidally effective amount of the above composition to the locus of crops, or other areas where insects are present or are expected to be present.

BRIEF DESCRIPTION OF THE DRAWINGS

FIG. 1 depicts the generic structure of compounds of formula I.

DETAILED DESCRIPTION OF THE INVENTION

The present invention generally relates to certain new and useful compounds, namely novel (heteroarylalkyl)alkane thio and oxo amine derivatives (hereinafter termed "compounds of formula I") as depicted in formula I:

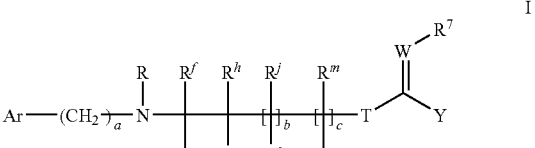

where
Ar is selected from

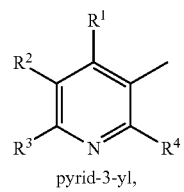

pyrid-3-yl,

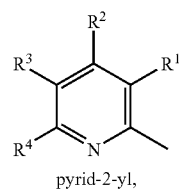

pyrid-2-yl,

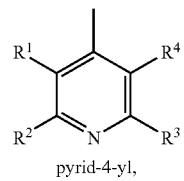

pyrid-4-yl,

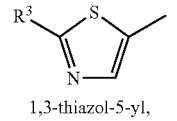

1,3-thiazol-5-yl,

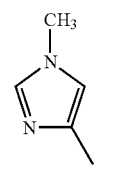

1-methyl-imidazol-4-yl,

-continued

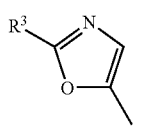
1,3-oxazol-5-yl,

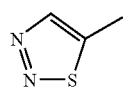
1,2,3-thiadiazol-5-yl,

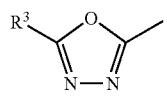
1,3,4-oxadiazol-2-yl,

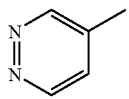
pyridazin-4-yl,

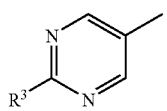
pyrimidin-5-yl,

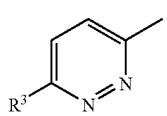
pyridazin-3-yl,

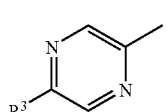
pyrazin-5-yl,

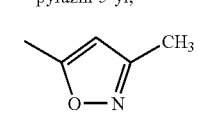
3-methyl-isoxazol-5-yl and

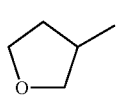
oxolan-3-yl where
$R^1$, $R^2$, $R^3$, and $R^4$ are independently selected from hydrogen, halogen, alkyl, alkoxy, haloalkyl, and haloalkoxy;
and,
a is an integer selected from 0 or 1;
R is selected from hydroxy, alkyl, haloalkyl, alkoxyalkyl, alkoxyalkoxyalkyl, cycloalkylalkyl, cyanoalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, cyclohex-1-en-3-yl, thien-3-ylmethyl, furan-2-ylmethyl, furan-3-ylmethyl, benzo[b]furan-2-ylmethyl, 2-$R^8$-1,3-thiazol-4-ylmethyl, 5-$R^8$-1,2,4-oxadiazol-3-ylmethyl,

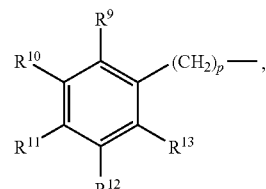
(1)

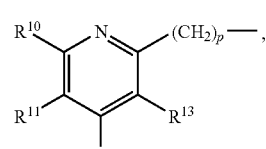
(2)

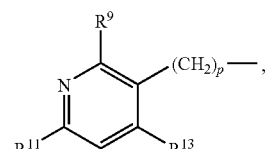
(3)

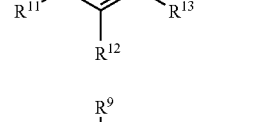
(4)

—$(CH_2)_p$—$CR^{14}$=$CR^{15}R^{16}$ and (5)

—$(CH_2)_p$—C≡$CR^{17}$, (6)

where
$R^8$ is selected from halogen, alkyl, aryl, and heteroaryl, wherein aryl and heteroaryl are optionally substituted with at least one of halogen, alkyl, haloalkyl, alkoxy, and haloalkoxy;
p is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyimino, dialkylaminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, alkyl and aryl;
$R^{17}$ is selected from hydrogen, alkyl,

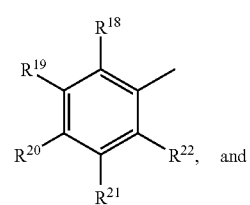
(7)

and

-continued (8)

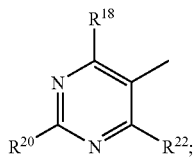

where

R[18], R[19], R[20], R[21], and R[22] are independently selected from hydrogen, halogen, alkyl, haloalkyl, alkoxy, and haloalkoxy;

b and c are integers independently selected from 0 or 1;

R[f], R[g], R[h], R[i], R[j], R[k], R[m] and R[n] are independently selected from hydrogen and alkyl;

T is selected from —O—, —S—, —CR[34]R[35]—;

Y is selected from —X—R[6] and;

(9)

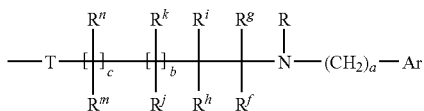

where

X is selected from —O—, —S—, and —CR[34]R[35]—;

R[6] is selected from hydrogen, alkyl, cycloalkyl, cycloalkylalkyl, alkoxy, alkoxyalkyl, alkoxyalkoxyalkyl, alkenyl, haloalkenyl, alkynyl and (10)

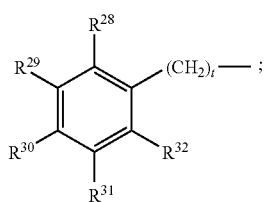

where t is an integer selected from 0, 1 and 2;

and,

R[28], R[29], R[30], R[31] and R[32] are independently selected from hydrogen, halogen, alkyl, haloalkyl, alkoxy, and haloalkoxy;

Ar, R, R[f], R[g], R[h], R[i], R[j], R[k], R[m], R[n], a, b and c have the same meaning as stated above;

R[7] is selected from —C≡N and —NO₂;

W is selected from —CR[33]— and —N—;

R[33], R[34], and R[35] are independently selected from hydrogen and alkyl;

where provided that when

I) i) Ar is pyrid-3-yl (A); ii) a is 1 and b and c are 0 and R[f] through R[i], inclusively, are hydrogen; iii) R is cycloalkylalkyl; iv) T is —S—; v) R[7] is —C≡N; and v) Y is

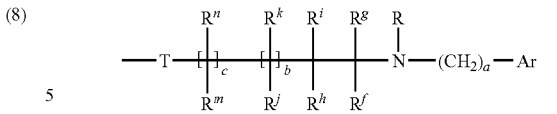

where Ar, R, R[f], R[g], R[h], R[i], a, b and c have the same meaning as stated above; vi) then W is —N—;

II) i) a is 1 and b and c are 0, and R[f] through R[i], inclusively, are hydrogen; ii) R is cyanoalkyl; iii) T is —S—; iv) W is v) R[7] is —C≡N; and vi) Y is

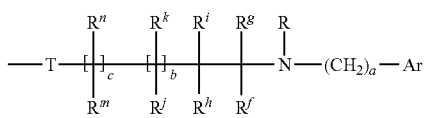

where Ar, R, R[f], R[g], R[h], R[i], a, b and c have the same meaning as stated above; vii) then Ar is other than 2-chloro-1,3-thiazol-5-yl;

the N-oxides thereof; and agriculturally acceptable salts thereof.

Preferred species are those compounds of formula I where a is 1; b and c are each 0; R[f], R[g], R[h] and R[i] are each hydrogen; W is selected from —CR[33]— and —N—, where R[33] is hydrogen; and T and X are each —S—;

More preferred species are those compounds of formula I where Ar is selected from (A)

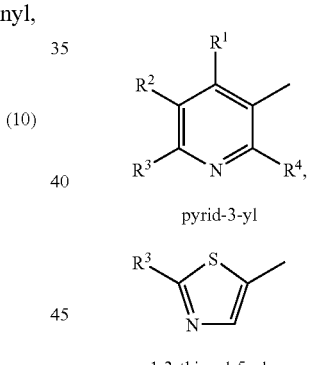

pyrid-3-yl (B)

and 1,3-thiazol-5-yl (M)

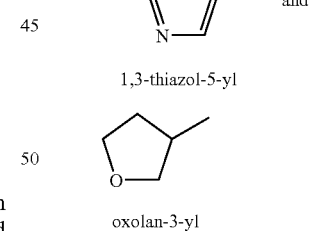

oxolan-3-yl where R[1], R[2] and R[4] are each hydrogen and R[3] is halogen.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one additional compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

The present invention also includes the use of the compounds and compositions set forth herein for control of non-agricultural insect, nematode and acarid species, for example, dry wood termites and subterranean termites; as well as for use as pharmaceutical agents and compositions thereof. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "cycloalkyl", used alone or as part of a larger moiety, includes cyclic rings of at least three carbon atoms and up to eight carbon atoms, more preferably three to six carbon atoms. The terms "haloalkyl" and "haloalkoxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein one or more hydrogen atoms have been replaced with halogen atoms, for example, trifluoromethyl or 2,2,2-trifluoroethoxy. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having four to ten carbon atoms, for example, phenyl, indanyl, indenyl, naphthyl or 5,6,7,8-tetrahydronaphthyl. The term "heteroaryl" refers to an aromatic ring structure, including fused rings, in which at least one of the atoms is other than carbon, for example, without limitation, sulfur, oxygen, or nitrogen. Heteroaryl rings include, without limitation, for example, oxazolyl, thiazolyl, imidazolyl, pyrazolyl, triazolyl or thiadiazolyl. The term "GC analysis" refers to gas chromatographic analysis of, for example, a chemical reaction mixture. The term "DMF" refers to N,N-dimethylformamide. The term "THF" refers to tetrahydrofuran. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The terms "insecticidal" or "acaricidal", "insecticide" or "acaricide" refers to a compound of the present invention, either alone or in admixture with at least one of an additional compound, or with at least one compatible carrier, which causes the destruction or the inhibition of action of insects or acarids. The term "independently selected from" as set forth above and in the claims section of the present specification refers to the possibility that moieties, for example the $R^1$ and $R^2$ substituents may be the same or they may be different within the group that the selection is made.

The novel compounds of formula I can be synthesized by methods that are individually known to one skilled in the art from intermediate compounds readily available in commerce.

Scheme 1 below illustrates a general procedure for synthesizing (heteroarylalkyl)alkane thio amine derivatives of formula I inter alia, where, for example Ar is pyrid-3-yl (A) substituted with $R^1$ through $R^4$; a is 1; $R^f$ through $R^i$, inclusively, are hydrogen; b and c are 0; W is —N—; $R^7$ is —CN; and Y is X—$R^6$:

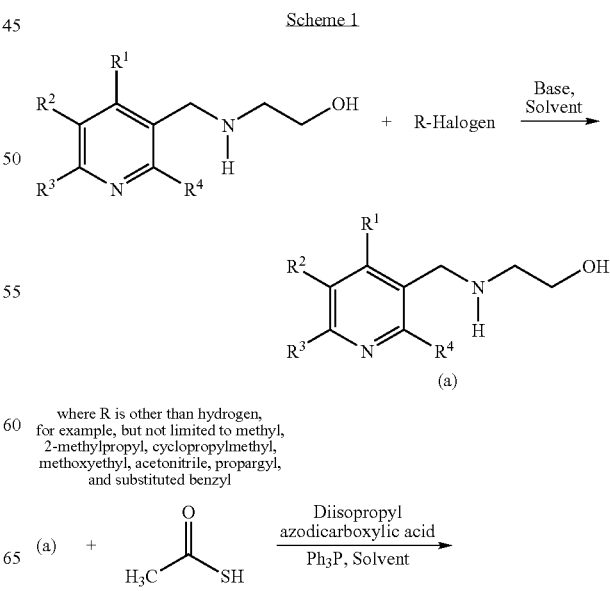

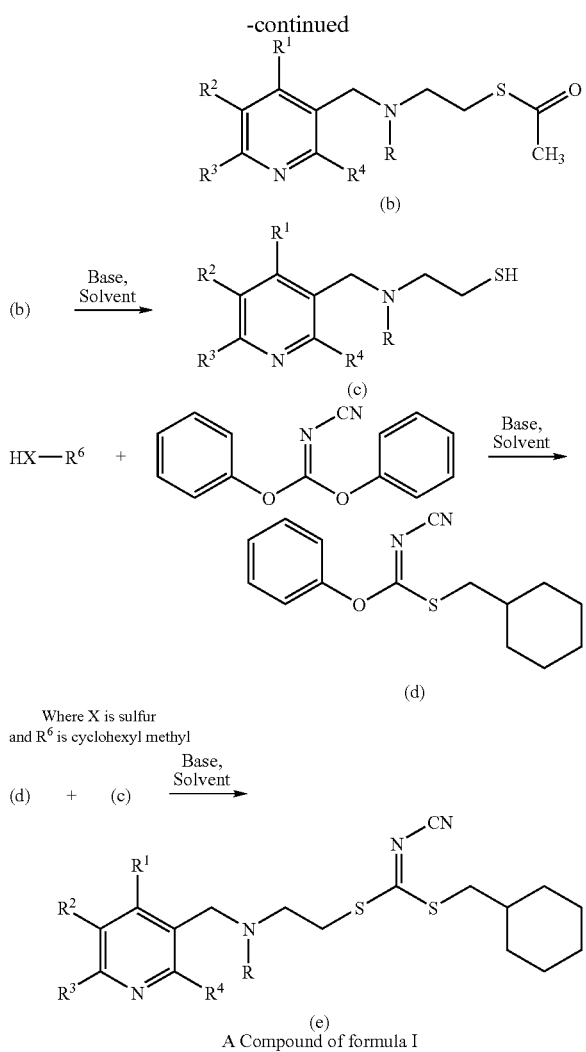

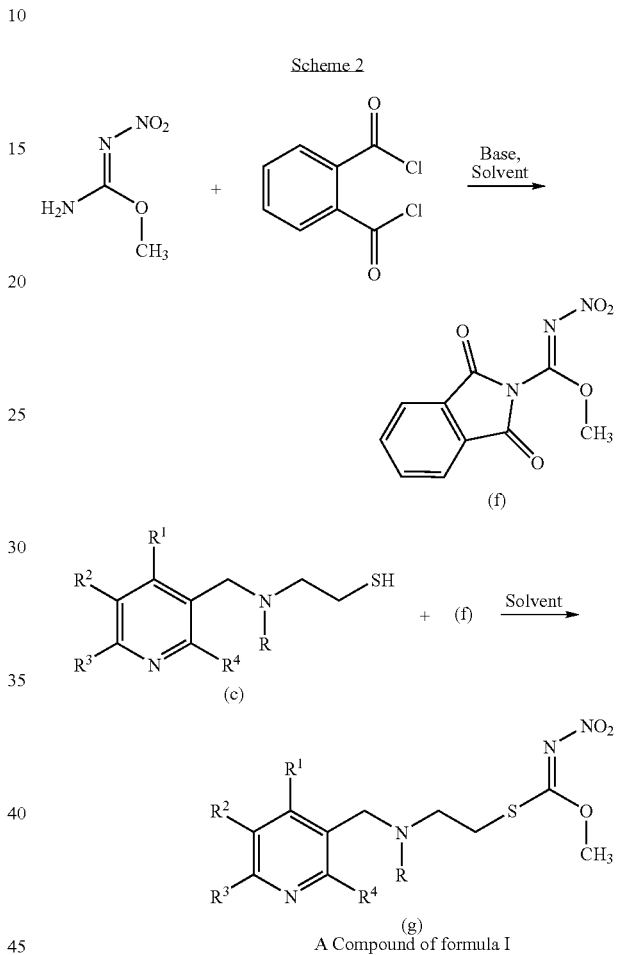

As depicted in Scheme 1, an appropriately substituted amino ethan-1-ol, for example, 2-{[(6-chloro(3-pyridyl))methyl]amino}ethan-1-ol (known compound, WO 2005/055715) was reacted with an alkyl or aryl halide, for example 1-iodo-2-methylpropane, under basic conditions yielding the corresponding tri-substituted amino ethan-1-ol (a), for example, 2-{[((6-chloro(3-pyridyl))methyl](2-methylpropyl)amino}ethan-1-ol. Intermediate (a) was treated with thiolacetic acid in the presence of triphenylphosphine and diisopropyl azodicarboxylic acid, providing the corresponding tri-substituted amino ethan-1-one (b), for example, 1-(2-{[((6-chloro(3-pyridyl))-methyl](2-methylpropyl)amino}ethylthio)ethan-1-one. Intermediate (b) was then treated with a base, such as methylamine, affording intermediate (c), for example, 2-{[((6-chloro(3-pyridyl))methyl](2-methylpropyl)amino}ethan-1-thiol. The reaction of a substituted thiol, for example, cyclohexylmethane-1-thiol, with diphenyl cyanocarbonimidate (commercially available from Aldrich Chemical Company) under basic conditions produced intermediate (d), for example, 2-aza-3-(cyclohexylmethylthio)-3-phenoxyprop-2-enenitrile. The reaction of intermediates (c) and (d) under basic conditions provided compounds of formula I (e), for example, 2-aza-3-(2-{[((6-chloro(3-pyridyl))methyl](2-methylpropyl)amino}ethylthio)-3-(cyclohexylmethylthio)prop-2-enenitrile. Example 1 set forth below provides in detail one method by which these compounds of formula I depicted in Scheme 1 are prepared.

Scheme 2 below illustrates a general procedure for synthesizing (heteroarylalkyl)alkane thio and oxo amine derivatives of formula I inter alia, where, for example Ar is pyrid-3-yl (A) substituted with $R^1$ through $R^4$; a is 1; $R^f$ through $R^i$, inclusively, are hydrogen; b and c are 0; W is —N—; and $R^7$ is —NO$_2$:

As depicted in Scheme 2, (1E)-2-aza-1-methoxy-2-nitrovinylamine (known compound, U.S. Pat. No. 6,124,466) was reacted under basic conditions with phthaloyl dichloride yielding intermediate (f), for example, 2-((1Z)-2-aza-1-methoxy-2-nitrovinyl)benzo[c]azoline-1,3-dione. Intermediate (c), prepared as set forth above as in Scheme 1 and Example 1, was then reacted under basic conditions with intermediate (f) yielding the corresponding compounds of formula I (g), for example, [2-((1E)-2-aza-1-methoxy-2-nitrovinylthio)ethyl][(6-chloro(3-pyridyl))methyl](2-methylpropyl)amine. Example 2 set forth below provides in detail one method by which compounds of formula I depicted in Scheme 2 are prepared.

Scheme 3 below illustrates another general procedure for synthesizing (heteroarylalkyl)alkane thio amine derivatives of formula I, inter alia, where, for example Ar is pyrid-3-yl (A) substituted with $R^1$ through $R^4$; a is 1; $R^f$ through $R^n$, inclusively, are hydrogen; b and c are 0; W is —CR$^{33}$— where $R^{33}$ is hydrogen; $R^7$ is —NO$_2$; and Y is X—R$^6$ or

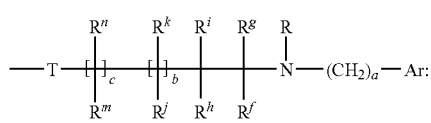

Scheme 3

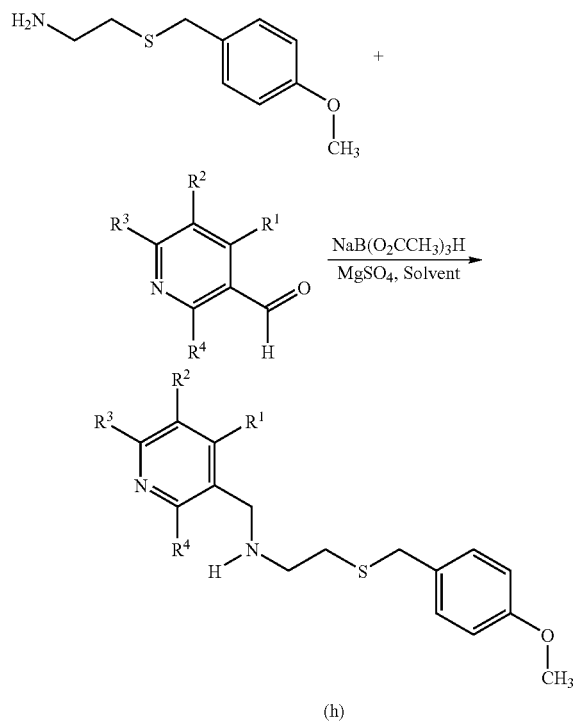

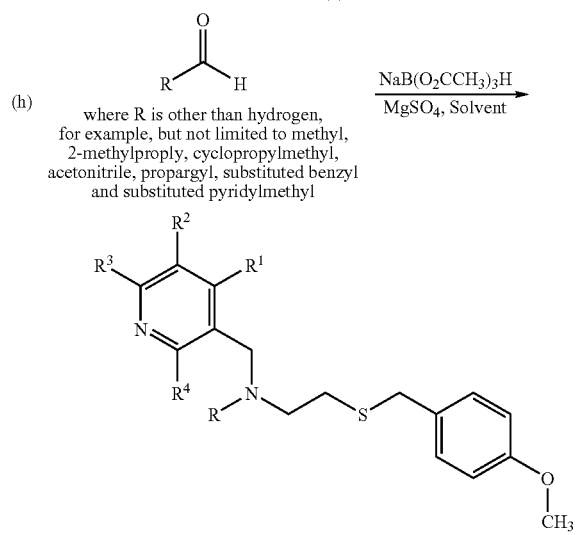

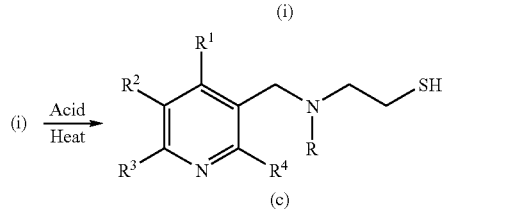

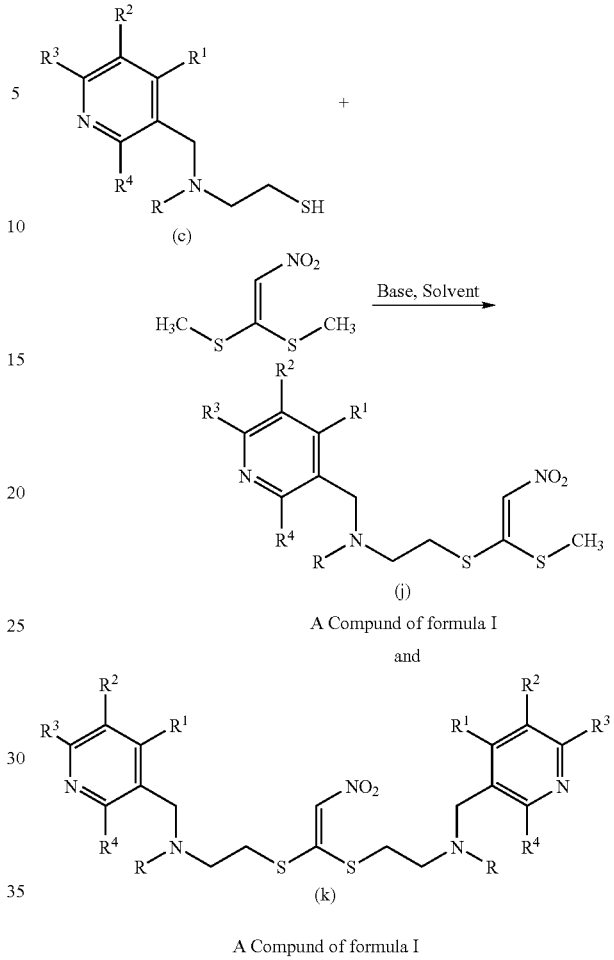

As depicted in Scheme 3, an appropriate (aryl)formaldehyde such as the known compound (6-chloro-3-pyridyl)formaldehyde, was condensed with a substituted (thioethyl)amine, for example the known compound 2-[(4-methoxyphenyl)methylthio]amine, then reduced with a reducing agent, such as sodium triacetoxyborohydride, yielding the corresponding intermediate (h), such as [(6-chloro(3-pyridyl))methyl]{[(4-methoxyphenyl)methylthio] ethyl}amine. A substituted formaldehyde, such as isobutyraldehyde, was condensed with intermediate (h), then reduced with a reducing agent, for example, sodium triacetoxyborohydride, affording the tri-substituted amine intermediate (i), for example, [(6-chloro(3-pyridyl))methyl]{[(4-methoxyphenyl)methylthio]-ethyl}(2-methylpropyl)amine. Intermediate (i) was heated in a strong acid, such as trifluoroacetic acid, forming the ethan-1-thiol intermediate of formula (c), for example, 2-{[((6-chloro(3-pyridyl))methyl](2-methylpropyl)amino}ethan-1-thiol. Intermediate (c) was then reacted with, 1,1-bis(methylthio)-2-nitroethylene (Aldrich Chemical Company), under basic conditions forming compounds of formula I (j), for example, [2-((1E)-1-methylthio-2-nitrovinylthio)ethyl][(6-chloro-(3-pyridyl))methyl](2-methylpropyl)amine and I(k), for example, {2-[1-(2-{[(6-chloro(3-pyridyl))-methyl}(2-methylpropyl) amino}ethylthio)ethyl}[6-chloro(3-pyridyl))methyl](2-methylpropyl)amine. Example 3 set forth below provides in detail the method by which compounds of formula I depicted in Scheme 3 were prepared.

Scheme 4 below illustrates another general procedure for synthesizing (heteroarylalkyl)alkane thio and oxo amine derivatives of formula I, inter alia, where, for example Ar is pyrid-3-yl (A) substituted with $R^1$ through $R^4$; a is 1; $R^f$ through $R^i$, inclusively, are hydrogen; b and c are 0:

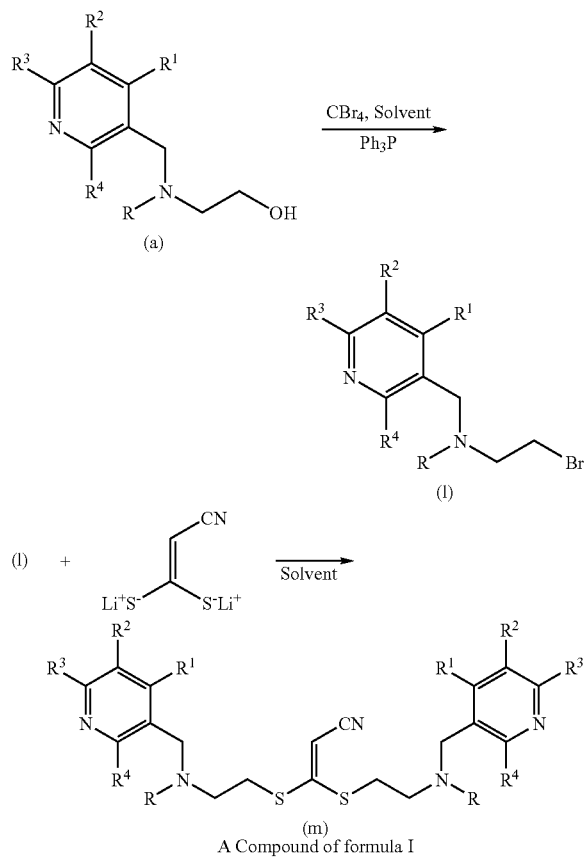

As depicted in Scheme 4, an intermediate of formula (a), prepared as set forth above in Scheme 1 in which R is, for example, methoxyethyl, was treated with carbon tetrabromide in the presence of triphenylphosphine yielding the brominated intermediate (l), for example (2-bromoethyl)[(6-chloro(3-pyridyl))methyl](2-methoxyethyl)amine. Stirring intermediate (l) with 3,3-dimercapto-2-propenenitrile, dilithium salt (known compound, U.S. Pat. No. 4,970,228) in an appropriate solvent, produced compounds of formula I (m), for example, 3,3-bis(2-{[(6-chloro(3-pyridyl))methyl](2-methoxyethyl)amino}ethylthio)prop2-enenitrile. Example 4 set forth below provides in detail the method by which these compounds of formula I depicted in Scheme 4 were prepared.

One skilled in the art will, of course, recognize that the formulation and mode of application of a toxicant may affect the activity of the material in a given application. Thus, for agricultural use the present insecticidal compounds may be formulated as a granule of relatively large particle size (for example, $\mathrm{^{3}/_{16}}$ or $\mathrm{^{4}/_{8}}$ US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal and acaricidal compounds of this invention may be formulated and/or applied with one or more additional compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with at least one additional compound, e.g., with other pesticides such as herbicides, the herbicides include, without limitation, for example: N-(phosphonomethyl)glycines such as glyphosate; aryloxyalkanoic acids such as 2,4-D, MCPA, and MCPP; ureas such as isoproturon; imidazolinones such as imazapyr, imazamethabenz, imazethapyr, and imazaquin; diphenyl ethers such as acifluorfen, bifenox, and fomasafen; hydroxybenzonitriles such as ioxynil and bromoxynil; sulfonylureas such as chlorimuron, achlorsulfuron, bensulfuron, pyrazosulfuron, thifensulfuron, and triasulfuron; 2-(4-aryloxyphenoxy)alkanoic acids such as fenoxaprop, fluazifop, quizalofop, and diclofop; benzothiadiazinones such as bentazone; 2-chloroacetanilides such as butachlor, metolachlor, acetochlor, and dimethenamide; arenecarboxylic acids such as dicamba; pyridyloxyacetic acids such as fluroxypyr, aryl triazolinones such as sulfentrazone and carfentrazone-ethyl; isoxazolidinones such as clomazone; and other herbicides.

When the active insecticidal compounds of the present invention are used in combination with at least one additional compound, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomehtrin, tefluthrin, cycloprothrin, betacyfluthrin, and acrinathrin; carbamate insecticides, such as aldicarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, imidacloprid, and other insecticides.

When the active insecticidal compounds of the present invention are used in combination with one or more of an additional compound, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with at least one additional compound, e.g., with other pesticides such as nematicides, the nematicides include, for example: carbofuran, carbosulfan, terbufos, aldecarb, ethoprop, fenamphos, oxamyl, isazofos, cadusafos, and other nematicides.

When the active insecticidal compounds of the present invention are used in combination with one or more of an additional compound, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

For veterinary use of the compounds of the invention in domestic and non-domestic animals, the compounds may be administered alone or in a formulation appropriate to the specific use envisaged and to the particular species of host animal being treated and the pest involved. The methods by which the compounds may be administered include oral administration by capsule, bolus, tablet or drench, or as a pour-on or spot-on formulation, or alternatively, they can be administered by injection (e.g. subcutaneously, intramuscularly or intravenously), dip, spray, mousse, shampoo, powder, or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution, which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from 0.01 to 10% by weight of the active ingredient.

These formulations will vary with regard to the weight of active compound contained therein depending on the species of host animal to be treated, the severity and type of infection and the body weight of the host. For parenteral, topical (e.g. using pour-on or spot-on, dip, spray, mousse, shampoo or powder to deliver the compound) and oral administration, typical dose ranges of the active ingredient are 0.01-100 mg per kg of body weight of the animal. Preferably the range is 0.1 to 10 mg per kg.

As an alternative the compounds may be administered with the animal feedstuff and for this purpose a concentrated feed additive or premix may be prepared for mixing with the normal animal feed.

The compounds of the invention may, in particular, be used in the field of veterinary medicine and livestock husbandry against arthropods, helminths or protozoa which are parasitic internally or externally upon vertebrates, particularly warm-blooded vertebrates, for example domestic and non-domestic animals, e.g. cattle, sheep, goats, equines, swine, poultry, dogs, and cats. The compounds of the invention are particularly useful in controlling arthropods, helminths or protozoa which are present inside the host animals or which feed in or on the skin or suck the blood of the animal, for which purpose they may be administered orally, parenterally, percutaneously or topically.

According to a further aspect of the invention, there is provided a pesticidal formulation comprising a compound of the invention, in admixture with a compatible adjuvant, diluent or carrier. Preferably, the formulation is adapted for topical administration.

The invention further provides a compound of the invention for use as a pesticide; and a method of treating a pest infestation at a locus, which comprises treatment of the locus with an effective amount of a compound of the invention. Preferably, the locus is the skin or fur of an animal.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of 2-aza-3-(2-{[(6-chloro(3-pyridyl))methyl](2-methylpropyl)amino}ethylthio)-3-(cyclohexylmethylthio)prop-2-ene (Compound 3-11)

Step A Synthesis of 2-{[(6-chloro(3-pyridyl))methyl](2-methylpropyl)amino}ethan-1-ol as an Intermediate A stirred mixture of 2.0 grams (0.007 mole) of 2-{[(6-chloro(3-pyridyl))methyl]amino}ethan-1-ol (known compound), 1.29 gram (0.007 mole) of 1-iodo-2-methylpropane and 0.9 gram (0.007 mole) if diisopropylethylamine in 50 mL of acetonitrile was heated at reflux for 16 hours. After this time the reaction mixture was concentrated under reduced pressure to a residue. The residue was purified by column chromatography on silica gel, eluting with a mixture of diethyl ether and hexanes. The appropriate fractions were combined and concentrated under reduced pressure, yielding 1.37 grams of 2-{[(6-chloro(3-pyridyl))methyl](2-methylpropyl)amino}ethan-1-ol. The NMR spectrum was consistent with the proposed structure.

Step B Synthesis of 1-(2-{[(6-chloro(3-pyridyl))methyl](2-methylpropyl)amino}-ethylthio)ethan-1-one as an Intermediate To a stirred, cold (0° C.) solution of 3.11 grams (0.012 mole) of triphenylphosphine in 200 mL of THF was added dropwise 2.28 grams (0.011 mole) of diisopropyl azodicarboxylate. The reaction mixture was stirred at 0° C. for five hours and at that time a solution of 1.37 grams (0.0056 mole) of 2-{[(6-chloro(3-pyridyl))methyl](2-methylpropyl)amino}ethan-1-ol and 0.94 gram (0.012 mole) of thiolacetic acid in 50 mL of THF was added dropwise. After complete addition the reaction mixture was stirred at 0° C. for one hour. The reaction mixture was concentrated under reduced pressure to a residue. The residue was purified by column chromatography on silica gel, eluting with mixtures of n-heptane and ethyl acetate. The appropriate fractions were combined and concentrated under reduced pressure, yielding 1.07 grams of the subject compound. The NMR spectrum was consistent with the proposed structure.

Step C Synthesis of 2-{[(6-chloro(3-pyridyl))methyl](2-methylpropyl)amino}ethane-1-thiol as an Intermediate A mixture of 0.25 gram (0.00083 mole) of 1-(2-{[(6-chloro(3-pyridyl))methyl](2-methylpropyl)-amino}ethylthio)

ethan-1-one and 0.78 gram of a 33% solution of methylamine in ethanol (0.0083 mole of methylamine) in 50 mL of ethanol was stirred at ambient temperature two hours. The reaction mixture was concentrated under reduced pressure to a residue. This residue was use without further purification in Step E.

Step D Synthesis of 2-aza-3-(cyclohexylmethylthio)-3-phenoxyprop-2-enenitrile as an Intermediate A solution of 2.86 grams (0.022 mole) of cyclohexylmethane-1-thiol (known compound) in 25 mL of acetonitrile was added dropwise to a stirred mixture of 10.66 rams (0.045 mole) of diphenyl cyanocarbonimidate (Aldrich Chemical Co.) and 2.89 grams (0.022 mole) of diisopropylethylamine in 50 mL of acetonitrile. The reaction mixture was stirred at ambient temperature for about 18 hours, and then concentrated under reduced pressure to a residue. The residue was purified by column chromatography on silica gel. Elution was accomplished using mixtures of n-heptane and methylene chloride. The appropriate fractions were combined and concentrated under reduced pressure, yielding 0.7 gram of 2-aza-3-(cyclohexylmethylthio)-3-phenoxyprop-2-enenitrile. The NMR spectrum was consistent with the proposed structure.

Step E Synthesis of 2-aza-3-(2-{[(6-chloro(3-pyridyl))methyl](2-methylpropyl)amino}-ethylthio)-3-(cyclohexylmethylthio)prop-2-ene (Compound 3-11)

A mixture of the residue prepared in Step C, 0.23 gram (0.00083 mole) of 2-aza-3-(cyclohexylmethylthio)-3-phenoxyprop-2-enenitrile and 0.11 gram (0.00083 mole) of diisopropylethylamine in 50 mL of acetonitrile was stirred at ambient temperature for about 18 hours, and then concentrated under reduced pressure to a residue. The residue was purified by column chromatography on silica gel. Elution was accomplished using mixtures of n-heptane and ethyl acetate. The appropriate fractions were combined and concentrated under reduced pressure, yielding 0.14 gram of 2-aza-3-(2-{[(6-chloro(3-pyridyl))methyl](2-methylpropyl)amino}ethylthio)-3-(cyclohexylmethylthio)prop-2-ene, Compound 3-11, as an oil. The NMR spectrum was consistent with the proposed structure.

EXAMPLE 2

This example illustrates one protocol for the preparation of [2-((1E)-2-aza-1-methoxy-2-nitrovinylthio)ethyl][(6-chloro(3-pyridyl))methyl](2-methylpropyl)amine (Compound 1-21)

Step A Synthesis of 2-{[(6-chloro(3-pyridyl))methyl](2-methylpropyl)amino}ethane-1-thiol as an Intermediate A mixture of 1.23 gram (0.0041 mole) of 1-(2-{[(6-chloro(3-pyridyl))methyl](2-methylpropyl)amino}ethylthio)ethan-1-one (prepared in a manner analogous to Example 1, Step B) and 3.8 grams of a 33% solution of methylamine in ethanol (0.041 mole of methylamine) in 10 mL of ethanol was stirred at ambient temperature one hour. The reaction mixture was concentrated under reduced pressure to a residue. The residue was purified by column chromatography on silica gel, eluting with mixtures of ethyl acetate and hexanes. The appropriate fractions were combined and concentrated under reduced pressure, yielding 0.99 gram of 2-{[(6-chloro(3-pyridyl))-methyl](2-methylpropyl)amino}ethane-1-thiol. The NMR spectrum was consistent with the proposed structure.

Step B Synthesis of 2-((1Z)-2-aza-1-methoxy-2-nitrovinyl)-4,5,6,7,3a,7a-hexahydroiso-indole-1,3-dione as an Intermediate To a solution of 0.65 gram (0.0055 mole) of 2-aza-1-methoxy-2-nitrovinylamine (known compound) and 1.29 gram (1.32 mL, 0.016 mole) of pyridine in 7 mL of methylene chloride was added dropwise 1.34 gram (0.95 mL, 0.0066 mole) of phthaloyl dichloride. The reaction mixture was stirred at ambient temperature for two hours. After this time the reaction mixture was cooled to 0° C., 0.2 mL of methanol was added and the mixture diluted with 16 mL of dilute aqueous hydrochloric acid (1N). The mixture was then extracted with methylene chloride. The extract was dried with sodium sulfate, filtered and the filtrate concentrated under reduced pressure, leaving a residue. The residue was subjected to column chromatography on silica gel. Elution was accomplished using mixtures of hexanes and ethyl acetate. Appropriate fractions were combined and concentrated under reduced pressure, yielding 0.35 gram of a mixture of the subject compound and 2-aza-1-methoxy-2-nitrovinylamine. The NMR spectrum indicated that the mixture consisted of about a 2:1 ratio of the subject compound and 2-aza-1-methoxy-2-nitrovinylamine.

Step C Synthesis of [2-((1E)-2-aza-1-methoxy-2-nitrovinylthio)ethyl][(6-chloro(3-pyridyl))methyl](2-methylpropyl)amine (Compound 1-21)

A stirred solution of 0.24 gram of the mixture prepared in Step B in 7 mL of methylene chloride was cooled to 0° C. and 0.24 gram (0.00094 mole) of 2-{[(6-chloro(3-pyridyl))methyl](2-methyl-propyl)amino}ethane-1-thiol was added. The reaction mixture was allowed to warm to ambient temperature where it was maintained during an 18 hour period. After this time the reaction mixture had become turbid and was filtered. Silica gel was added to the filtrate and the mixture was concentrated under reduced pressure to a residue. The residue was subjected to several column chromatography purifications on silica gel, combining the appropriate fractions and concentrating prior to the next purification, eluting with the following: first purification, mixtures of ethyl acetate and hexanes; second purification, methylene chloride; third purification, mixtures of ethyl acetate and hexanes. The third chromatography purification provided 0.06 gram of [2-((1E)-2-aza-1-methoxy-2-nitrovinylthio)ethyl][(6-chloro(3-pyridyl))methyl](2-methylpropyl)-amine, Compound 1-21, as an oil. The NMR spectrum was consistent with the proposed structure.

EXAMPLE 3

This example illustrates one protocol for the preparation of [2-((1E)-1-methylthio-2-nitrovinylthio)ethyl][(6-chloro(3-pyridyl))methyl](2-methylpropyl)amine (Compound 2-4) and {2-[1-(2-{[(6-chloro(3-pyridyl))methyl}(2-methylpropyl)amino}ethylthio)-2-nitrovinylthio]ethyl}[6-chloro(3-pyridyl))methyl](2-methylpropyl)amine (Compound 2-15)

Step A Synthesis of [(6-chloro(3-pyridyl))methyl]{2-[(4-methoxyphenyl)methylthio]-ethyl}amine as an Intermediate Under a dry nitrogen atmosphere, a mixture of 8.0 grams (0.041 mole) of 2-[(4methoxyphenyl)-methylthio]ethylamine (known compound), 5.7 grams (0.041 mole) of 6-chloropyridine-3-carbaldehyde and 9.7 grams (0.081 mole) of magnesium sulfate in 160 mL of 1,2-dichloroethane was stirred at ambient temperature for about five hours. Sodium triacetoxyborohydride (12.9 grams, 0.061 mole) was added and the reaction mixture stirred at ambient temperature for about 18 hours. After this time 200 mL of an aqueous 5% sodium carbonate solution was added and the mixture stirred for two hours. The mixture was filtered and the filter cake rinsed with methylene chloride. The filtrate and rinse were combined and extracted with three portions of methylene chloride. The combined extracts were dried with sodium sulfate and filtered. The filtrate was concentrated under reduced pressure to a yellow oil. The oil was subjected to several column chromatography purifications on silica gel, combining the appropriate fractions and concentrating prior to the next purification, eluting with mixtures of methylene chloride and methanol. The third chromatography purification provided 9.39 grams of [(6-chloro(3-pyridyl))methyl]{2-[(4-methoxyphenyl)methylthio]ethyl}amine as an oil. The NMR spectrum was consistent with the proposed structure.

Step B Synthesis of [(6-chloro(3-pyridyl))methyl]{2-[(4-methoxyphenyl)methylthio]-ethyl}(2-methylpropyl)amine as an Intermediate This compound was made in a manner analogous to that set forth in Step A of Example 3, using 2.0 grams (0.0062 mole) of [(6-chloro(3-pyridyl))methyl]{2-[(4-methoxyphenyl)methylthio]ethyl}-amine, 0.45 gram (0.0062 mole) of isobutyraldehyde, 2.0 gram (0.0093 mole) of sodium triacetoxyborohydride and 1.5 grams (0.0124 mole) of magnesium sulfate in 40 mL of 1,2-dichloroethane. The yield of the subject compound after one column chromatography purification on silica gel, eluting with a mixture of ethyl acetate and hexanes, was 2.05 grams. The NMR spectrum was consistent with the proposed structure.

Step C Synthesis of 2-{[(6-chloro(3-pyridyl)methyl](2-methylpropyl)amino}ethan-1-thiol as an Intermediate Under a dry nitrogen atmosphere a stirred solution of 1.25 gram (0.0033 mole) of [(6-chloro(3-pyridyl))methyl]{2-[(4-methoxyphenyl)methylthio]ethyl}(2-methylpropyl)amine in 25 mL of trifluoroacetic acid was heated at 70° for six hours, and then was allowed to cool to ambient temperature where it stirred for about 18 hours. After this time the reaction mixture was concentrated and dissolved in methylene chloride to which 50 mL of an aqueous 5% potassium carbonate solution was added. The mixture was stirred for 10 minutes and was extracted with two portions of methylene chloride. The extracts were combined, dried with sodium sulfate and filtered. The filtrate was concentrated under reduced pressure to a semi-solid residue. The residue was purified by column chromatography on silica gel eluting with mixtures of hexanes and ethyl acetate, yielding 0.31 gram of the subject compound. The NMR spectrum was consistent with the proposed structure.

Step D Synthesis of [2-((1E)-1-methylthio-2-nitrovinylthio)ethyl][(6-chloro(3-pyridyl))-methyl](2-methylpropyl)amine (Compound 2-4) and {2-[1-(2-{[(6-chloro(3-pyridyl))methyl](2-methylpropyl)amino}ethylthio)-2-nitrovinylthio]ethyl}[6-chloro(3-pyridyl))methyl](2-methylpropyl)amine (Compound 2-15)

Under a dry nitrogen atmosphere a stirred mixture of 0.30 gram (0.0012 mole) of 2-{[(6-chloro(3-pyridyl))methyl](2-methylpropyl)amino}ethane-1-thiol, 0.21 gram (0.0013 mole) of 1,1-bis-(methylthio)-2-nitroethylene and 0.19 gram (0.0015 mole) of diisopropylethylamine in 30 mL of acetonitrile was heated at 80° C. for three hours and then cooled to ambient temperature where it stirred for about 18 hours. After this time 1.2 grams of silica gel was added and the mixture was concentrated under reduced pressure to a residue. The residue was subjected to two column chromatography purifications on silica gel, combining the appropriate fractions and concentrating prior to the next purification, eluting with the following: first purification, mixtures of methylene chloride and hexanes followed by mixtures of methylene chloride and methanol; second purification, mixtures of hexanes and diethyl ether. The appropriate fractions were combined and concentrated under reduced pressure to yield two compounds: 0.04 gram of {2-[1-(2-{[(6-chloro(3-pyridyl))methyl}(2-methylpropyl)amino}ethylthio)-2-nitrovinylthio]ethyl}[6-chloro(3-pyridyl))-methyl](2-methylpropyl)amine, Compound 2-15, as an oil and 0.11 gram of [2-((1E)-1-methylthio-2-nitrovinylthio)ethyl][(6-chloro(3-pyridyl))methyl](2-methylpropyl)amine, Compound 2-4, as an oil. The NMR spectra were consistent with the proposed structures.

EXAMPLE 4

This example illustrates one protocol for the preparation of 3,3-bis(2-{[(6-chloro(3-pyridyl))-methyl](2-methoxyethyl)amino}ethylthio)prop-2-enenitrile (Compound 4-2)

Step A Synthesis of 2-{[(6-chloro(3-pyridyl))methyl](2-methoxyethyl)amino}ethan-1-ol as an Intermediate A stirred mixture of 6.0 grams (0.03 mole) of 2-{[(6-chloro(3-pyridyl))methyl]amino}ethan-1-ol (known compound), 4.6 grams (0.033 mole) of 2-bromoethyl methyl ether and 5.8 grams (0.045 mole) if diisopropylethylamine in 120 mL of 1,4-dioxane was heated at 95° C. for 36 hours. After this time the reaction mixture was cooled to ambient temperature and was concentrated under reduced pressure to a residue. The residue was purified by column chromatography on silica gel, eluting with a mixture of methanol and methylene chloride. The appropriate fractions were combined and concentrated under reduced pressure, yielding 4.3 grams of 2-{[(6-chloro(3-pyridyl))methyl](2-methoxyethyl)amino}ethan-1-ol as an oil. The NMR spectrum was consistent with the proposed structure.

Step B Synthesis of (2-bromoethyl)[(6-chloro(3-pyridyl))methyl](2-methoxyethyl)amine as an Intermediate To a cold (0° C.) solution of 1.25 grams (0.0051 mole) of 2-{[(6-chloro(3-pyridyl)methyl](2-methoxyethyl)amino}ethan-1-ol and 1.9 grams (0.0057 mole) of carbon tetrabromide in 70 mL of methylene chloride was added 1.66 grams (0.0064 mole) of triphenylphosphine. The reaction mixture was allowed to warm to ambient temperature where it stirred for 1.5 hours. After this time silica gel was added and the mixture concentrated under reduced pressure to a residue. The residue was subjected to column chromatography on silica gel eluting with a 50/50 mixture of diethyl ether and hexanes. The appropriate fractions were combined and concentrated under reduced pressure, yielding 1.17 grams of (2-bromoethyl)[(6-chloro(3-pyridyl))methyl](2-methoxyethyl)amine as an oil. The NMR spectrum was consistent with the proposed structure.

Step C Synthesis of 3,3-bis(2-{[(6-chloro(3-pyridyl))methyl](2-methoxyethyl)amino}-ethylthio)prop-2-enenitrile (Compound 4-2)

A stirred mixture of 1.17 gram (0.0038 mole) of (2-bromoethyl)[(6-chloro(3-pyridyl))methyl](2-methoxyethyl)amine and 0.37 gram (0.0038 mole) of 3,3-dimercapto-3-propenenitrile, dilithium salt in 10 mL of DMF was heated at 50° C. for 24 hours. The reaction mixture was allowed to cool and was concentrated under reduced pressure to a residue. The residue was diluted with 50 mL of aqueous saturated sodium chloride solution and the mixture was extracted with 100 mL of ethyl acetate. The extract was dried with sodium sulfate, and filtered. Silica gel was added to the filtrate and the mixture was concentrated under reduced pressure to a residue. The residue was subjected to column chromatography on silica gel eluting with a 50/50 mixture of diethyl ether and ethyl acetate, yielding 0.6 gram of 3,3-bis(2-{[(6-chloro(3-pyridyl))methyl](2-methoxyethyl)-amino}ethylthio)prop-2-enenitrile, Compound 4-2, as an oil. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some additional examples of compounds of formula I useful in the present invention:

TABLE 1

Insecticidal (Heteroarylalkyl)alkyl Thio and Oxo Amine Derivatives

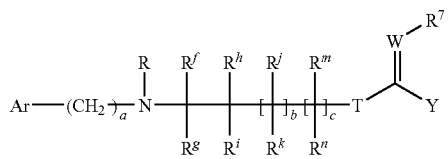

I wherein

Ar is selected from

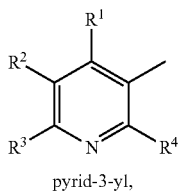

pyrid-3-yl, (A)

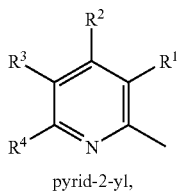

pyrid-2-yl, (A1)

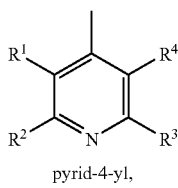

pyrid-4-yl, (A2)

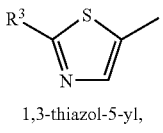

1,3-thiazol-5-yl, (B)

TABLE 1-continued
Insecticidal (Heteroarylalkyl)alkyl Thio and Oxo Amine Derivatives
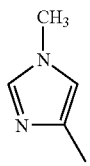
1-methyl-
imidazol-4-yl, (C)
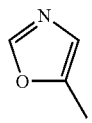
1,3-oxazol-5-yl, (D)
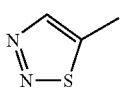
1,2,3-thiadiazol-
5-yl, (E)
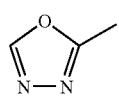
1,3,4-oxadiazol-
2-yl, (F)
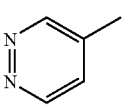
pyridazin-4-yl, (G)
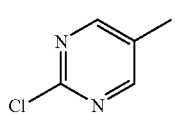
2-chloro-
pyrimidin-5-yl, (H)
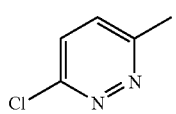
6-chloro-
pyridazin-3-yl, (J)
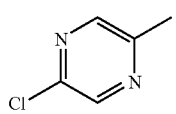
2-chloropyrazin-
5-yl, (K)
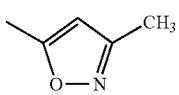
3-methylisoxazol-5-yl, and (L)

TABLE 1-continued
Insecticidal (Heteroarylalkyl)alkyl Thio and Oxo Amine Derivatives
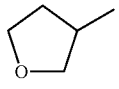
oxolan-3-yl;
(M)
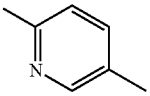
I-1
| Cmpd. No. | b | Ar | R | Y |
|---|---|---|---|---|
| 1-1 | 0 | 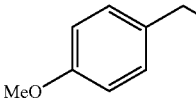 | 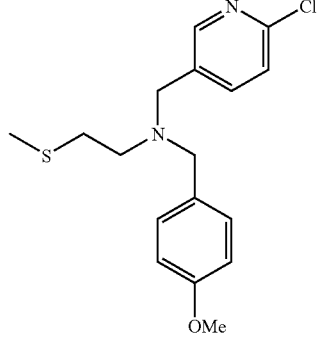 | 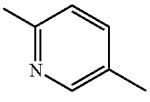 |
| 1-2 | 0 | 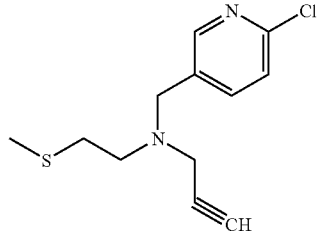 | —CH$_2$C≡CH | 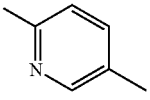 |
| 1-3 | 0 | 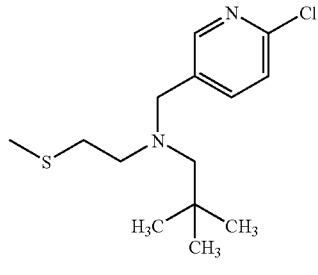 | —CH$_2$C(CH$_3$)$_3$ | 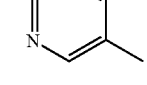 |
| 1-4 | 0 | 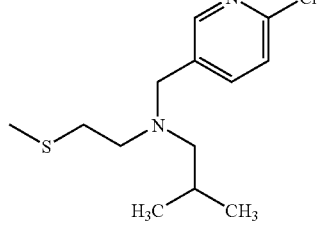 | —CH$_2$CH(CH$_3$)$_2$ | |

TABLE 1-continued
Insecticidal (Heteroarylalkyl)alkyl Thio and Oxo Amine Derivatives
| 1-5 | O | 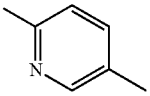 |  | 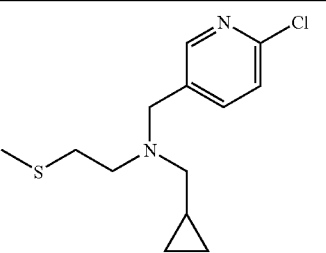 |
| 1-6 | O | 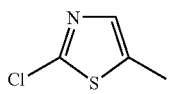 | —CH$_2$C≡CH | 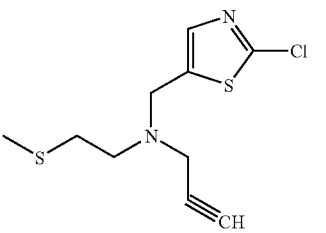 |
| 1-7 | O | 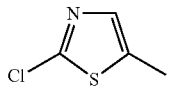 | —CH$_2$CH(CH$_3$)$_2$ | 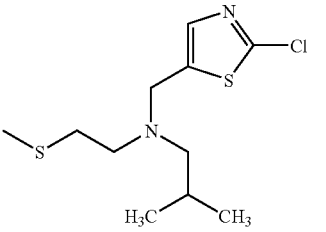 |
| 1-8 | O | 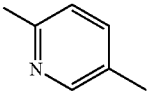 | —CH$_2$C≡N | 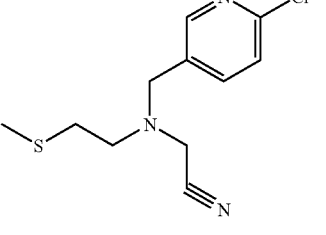 |
| 1-9 | O | 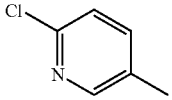 | 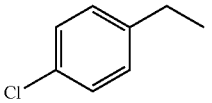 | —SCH$_3$ |
| 1-10 | O | 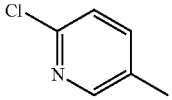 | 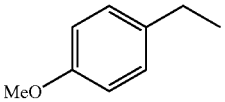 | —SCH$_3$ |
| 1-11 | O | 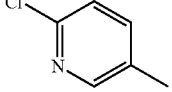 | —CH$_3$ | —SCH$_3$ |
| 1-12 | O | 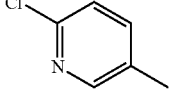 | —CH$_2$C≡CH | —SCH$_3$ |
| 1-13 | O | 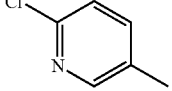 | —CH$_2$C(CH$_3$)$_3$ | —SCH$_3$ |

TABLE 1-continued
Insecticidal (Heteroarylalkyl)alkyl Thio and Oxo Amine Derivatives
| | | | | |
|---|---|---|---|---|
| 1-14 | 0 | 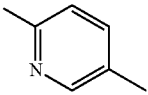 | —CH$_2$CH(CH$_3$)$_2$ | —SCH$_3$ |
| 1-15 | 0 | 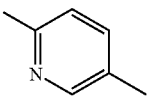 | 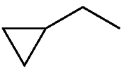 | —SCH$_3$ |
| 1-16 | 0 | 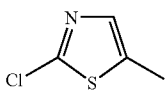 | —CH$_2$C≡CH | —SCH$_3$ |
| 1-17 | 0 | 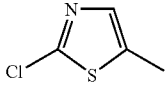 | —CH$_2$CH(CH$_3$)$_2$ | —SCH$_3$ |
| 1-18 | 0 | 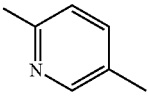 | —CH$_2$C≡N | —SCH$_3$ |
| 1-19 | 1 | 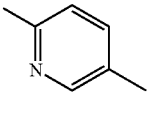 | —CH$_2$C≡CH | —SCH$_3$ |
| 1-20 | 1 | 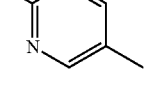 | —CH$_2$C≡CH | 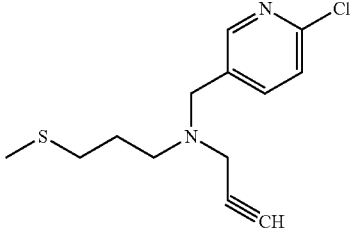 |
| 1-21 | 0 | 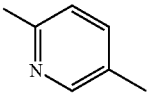 | —CH$_2$CH(CH$_3$)$_2$ | —OCH$_3$ |
| 1-22 | 0 | 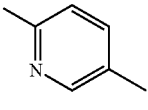 | —CH$_2$CH(CH$_3$)$_2$ | 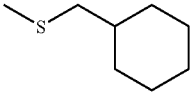 |
| 1-23 | 0 | 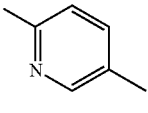 | —CH$_2$CH(CH$_3$)$_2$ | —SCH$_2$C(CH$_3$)$_3$ |

TABLE 1-continued

Insecticidal (Heteroarylalkyl)alkyl Thio and Oxo Amine Derivatives

I-2

| Cmpd. No. | b | Ar | R | Y |
|---|---|---|---|---|
| 2-1 | 0 | 2-chloro-5-pyridyl | 4-chlorobenzyl | N-((6-chloropyridin-3-yl)methyl)-N-(4-chlorobenzyl)-2-(methylthio)ethanamine |
| 2-2 | 0 | 2-chloro-5-pyridyl | —CH₂C≡CH | N-((6-chloropyridin-3-yl)methyl)-N-(prop-2-yn-1-yl)-2-(methylthio)ethanamine |
| 2-3 | 0 | 2-chloro-5-pyridyl | 4-methoxybenzyl | N-((6-chloropyridin-3-yl)methyl)-N-(4-methoxybenzyl)-2-(methylthio)ethanamine |
| 2-4 | 0 | 2-chloro-5-pyridyl | —CH₂CH(CH₃)₂ | N-((6-chloropyridin-3-yl)methyl)-N-isobutyl-2-(methylthio)ethanamine |

TABLE 1-continued
Insecticidal (Heteroarylalkyl)alkyl Thio and Oxo Amine Derivatives
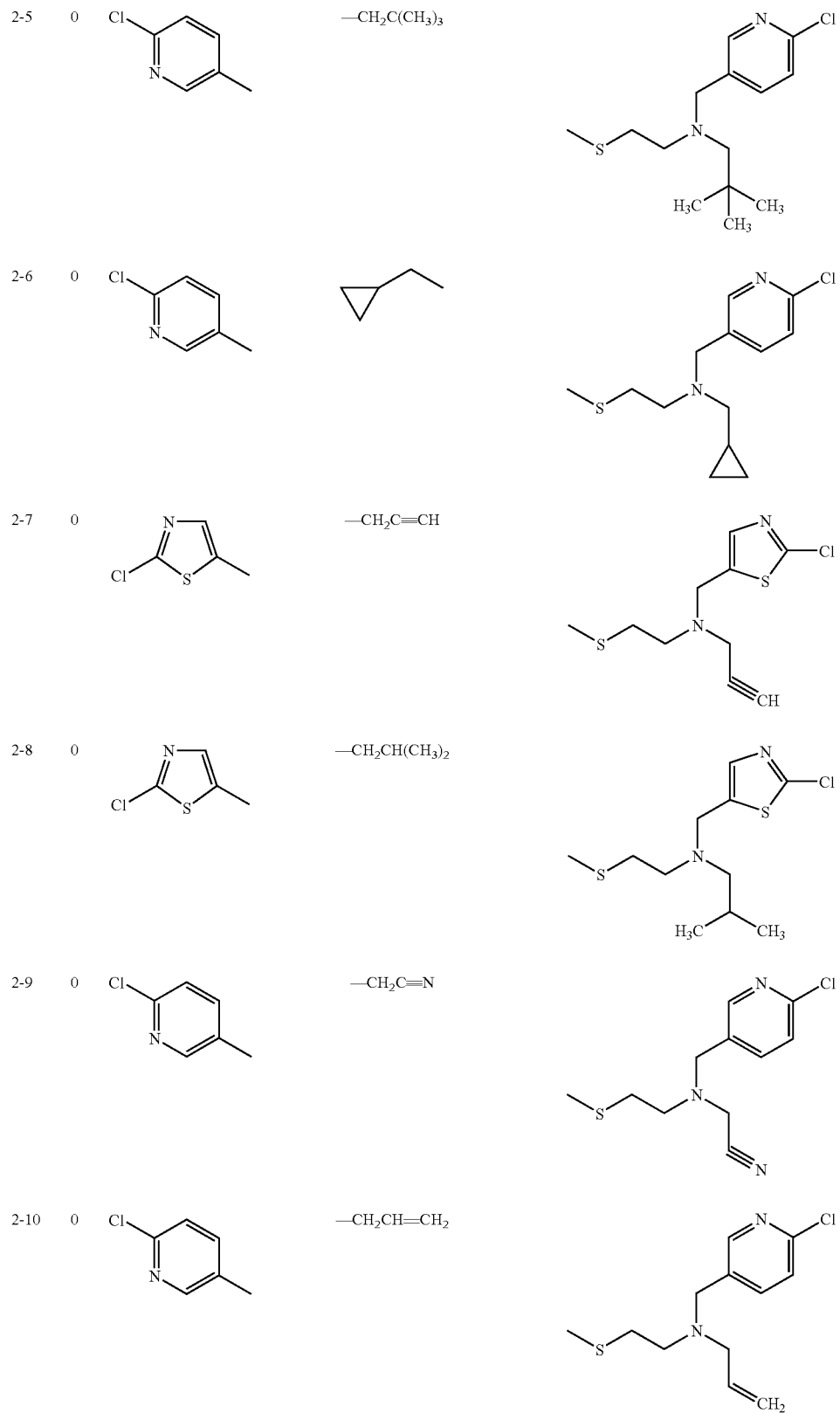

TABLE 1-continued
Insecticidal (Heteroarylalkyl)alkyl Thio and Oxo Amine Derivatives
| | | | | |
|---|---|---|---|---|
| 2-11 | 0 | 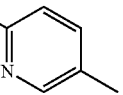 | —CH₃ | —SCH₃ |
| 2-12 | 0 | 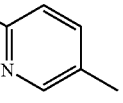 | 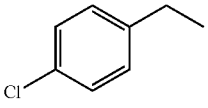 | —SCH₃ |
| 2-13 | 0 | 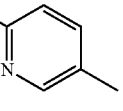 | —CH₂C≡CH | —SCH₃ |
| 2-14 | 0 | 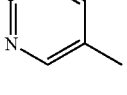 | 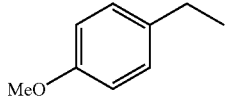 | —SCH₃ |
| 2-15 | 0 | 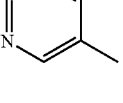 | —CH₂CH(CH₃)₂ | —SCH₃ |
| 2-16 | 0 | 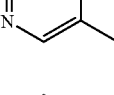 | —CH₂C(CH₃)₃ | —SCH₃ |
| 2-17 | 0 | 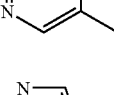 | 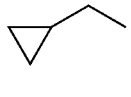 | —SCH₃ |
| 2-18 | 0 | 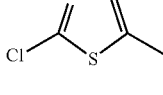 | —CH₂C≡CH | —SCH₃ |
| 2-19 | 0 | 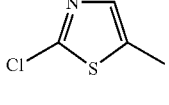 | —CH₂CH(CH₃)₂ | —SCH₃ |
| 2-20 | 0 | 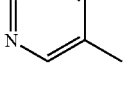 | —CH₂C≡N | —SCH₃ |
| 2-21 | 0 | 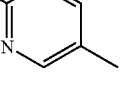 | —CH₂CH=CH₂ | —SCH₃ |
| 2-22 | 1 | 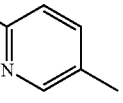 | —CH₂C≡CH | —SCH₃ |

TABLE 1-continued
Insecticidal (Heteroarylalkyl)alkyl Thio and Oxo Amine Derivatives
| Cmpd. No. | b | Ar | | Y |
|---|---|---|---|---|
| 2-23 | 1 | 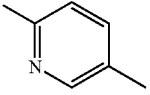 | —CH₂C≡CH | 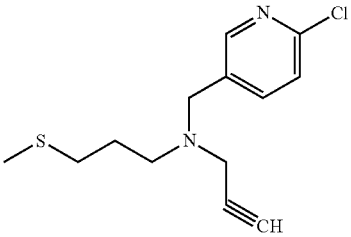 |
| 2-24 | 0 | 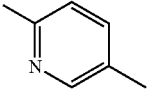 | —CH₂C≡CH | 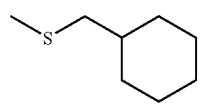 |
| 2-25 | 0 | 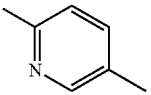 | —CH₂CH=CCl₂ | —SCH₃ |
| 2-26 | 0 | 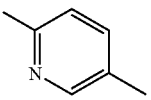 | —CH₂CH=CH₂ | 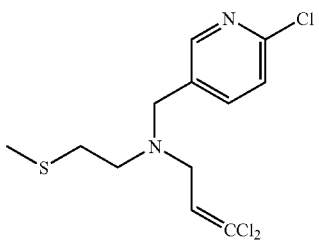 |
| 2-27 | 0 | 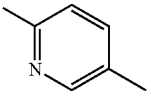 | —CH₂CH(CH₃)₂ | 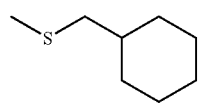 |
| 2-28 | 0 | 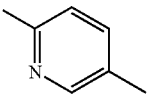 | —CH₂CH(CH₃)₂ | —CH₂C(CH₃)₃ |
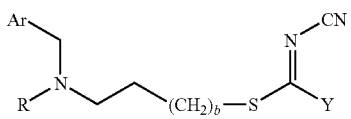
I-3
| Cmpd. No. | b | Ar | R | Y |
|---|---|---|---|---|
| 3-1 | 0 | 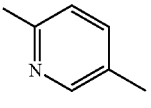 | 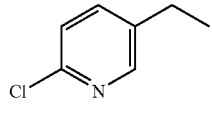 | 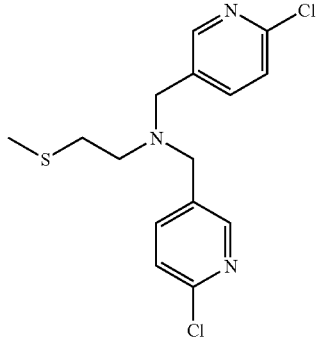 |

TABLE 1-continued
Insecticidal (Heteroarylalkyl)alkyl Thio and Oxo Amine Derivatives
| | | | | |
|---|---|---|---|---|
| 3-2 | 0 | 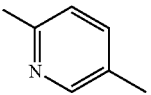 | —CH₂C≡CH | 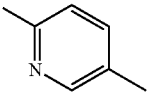 |
| 3-3 | 0 | 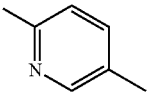 | —CH₂CH(CH₃)₂ | 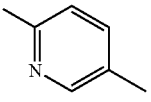 |
| 3-4 | 0 | 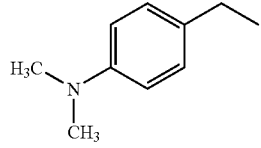 | —CH(CH₃)₂ | 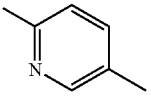 |
| 3-5 | 0 | 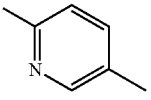 | 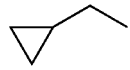 | 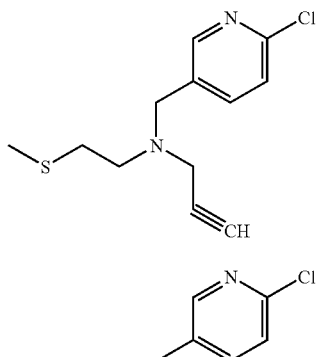 |
| 3-6 | 0 | 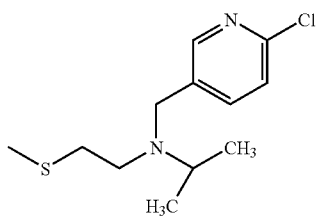 | —CH₂CH₂OCH₃ | 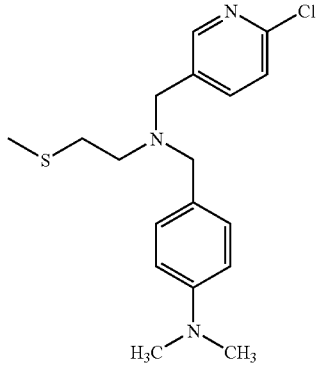 |
| 3-7 | 0 | 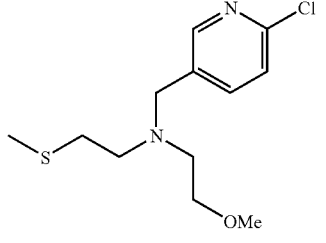 | 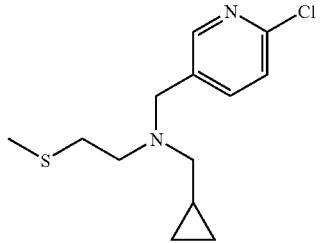 | |

TABLE 1-continued
Insecticidal (Heteroarylalkyl)alkyl Thio and Oxo Amine Derivatives
| | | | | |
|---|---|---|---|---|
| 3-8 | O | 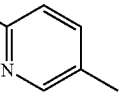 | 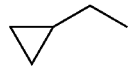 | 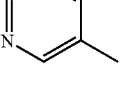 |
| 3-9 | O | 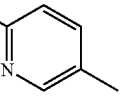 | —CH$_2$CH$_2$OCH$_3$ | 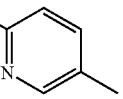 |
| 3-10 | O | 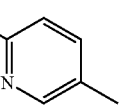 | —CH$_2$C≡CH | 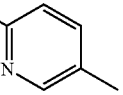 |
| 3-11 | O | 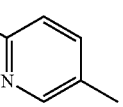 | —CH$_2$CH(CH$_3$)$_2$ | 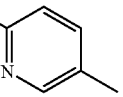 |
| 3-12 | O |  | —CH$_2$CH$_2$OCH$_3$ | —SCH$_2$C(CH$_3$)$_3$ |
| 3-13 | O | 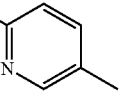 | 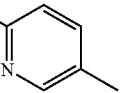 | —SCH$_2$C(CH$_3$)$_3$ |
| 3-14 | O | 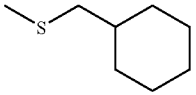 | —CH$_2$CH(CH$_3$)$_2$ | —SCH$_2$C(CH$_3$)$_3$ |
| 3-15 | O | 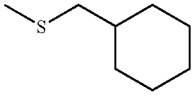 | —CH$_2$C≡N | 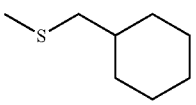 |
| 3-16 | O | 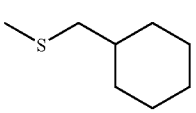 | —CH$_2$C≡CH | 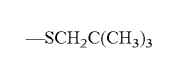 |
| 3-17 | O | 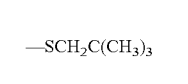 | —CH$_2$C≡CH | —SCH$_2$C≡CH |
| 3-18 | O | 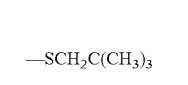 | —CH$_2$C≡CH |  |

TABLE 1-continued
Insecticidal (Heteroarylalkyl)alkyl Thio and Oxo Amine Derivatives
| 3-19 | 0 | 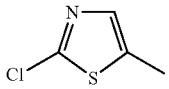 | —CH$_2$C≡CH | 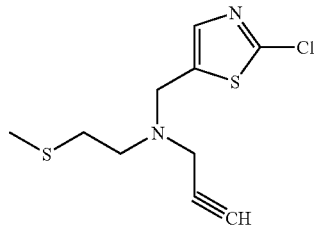 |
| --- | --- | --- | --- | --- |
| 3-20 | 0 | 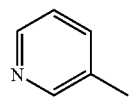 | —CH$_2$C≡CH | 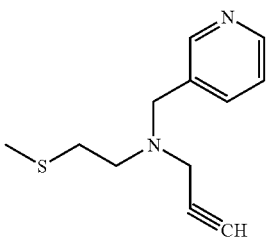 |
| 3-21 | 0 | 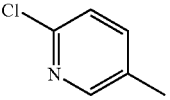 | —CH$_2$C≡CH | —SCH$_3$ |
| 3-22 | 0 | 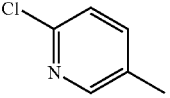 | —CH$_2$C≡CH | —SCH$_2$CH$_2$CH=CF$_2$ |
| 3-23 | 0 | 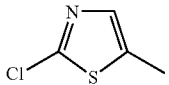 | 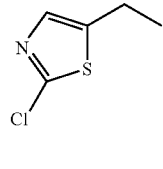 | 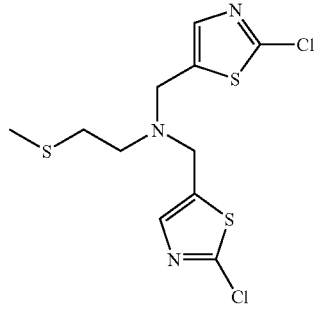 |
| 3-24 | 1 | 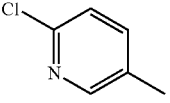 | —CH$_2$C≡CH | 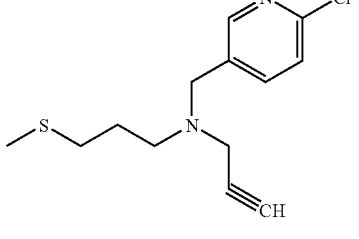 |
| 3-25 | 0 | 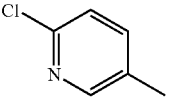 | —CH$_2$C≡CH | —CH$_3$ |
| 3-26 | 0 |  | 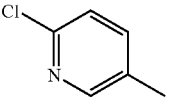 | —CH$_3$ |

TABLE 1-continued
Insecticidal (Heteroarylalkyl)alkyl Thio and Oxo Amine Derivatives
| 3-27 | 0 | 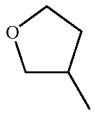 | —CH$_2$C≡CH | 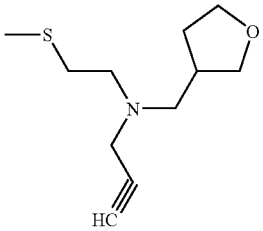 |
| 3-28 | 0 | 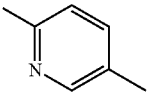 | —CH$_2$CH=CCl$_2$ | 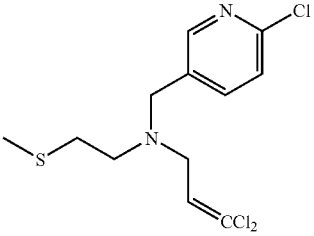 |
| 3-29 | 0 | 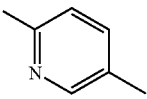 | —CH$_2$C≡CH | —SCH$_2$CH$_2$C(CH$_3$)$_3$ |
| 3-30 | 0 | 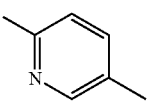 | —CH$_2$C≡CH | 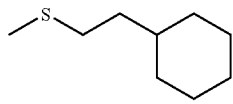 |
| 3-31 | 0 | 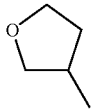 | —CH$_2$C≡N | 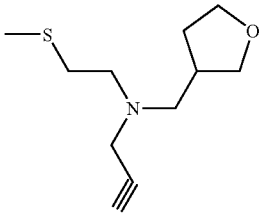 |
| 3-32 | 0 | 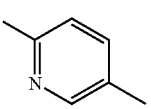 | —CH$_2$CH=CH$_2$ | 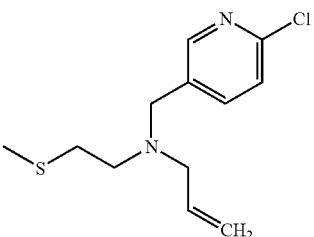 |
| 3-33 | 1 |  | —CH$_2$C≡N | 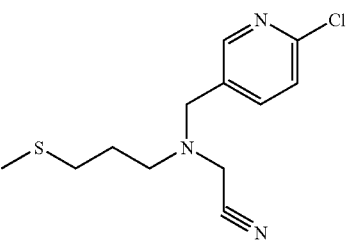 |
| 3-34 | 0 | 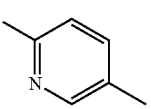 | —CH$_2$C≡CH | —SCH$_2$C≡CH |

TABLE 1-continued

Insecticidal (Heteroarylalkyl)alkyl Thio and Oxo Amine Derivatives

| Cmpd. No. | | | | |
|---|---|---|---|---|
| 3-35 | 0 | Cl-pyridine-CH₃ | —CH₂C≡CH | —SCH₂CH(CH₃)₂ |
| 3-36 | 0 | Cl-pyridine-CH₃ | —CH₂C≡CH | —SCH₂CH₂OCH₃ |
| 3-37 | 0 | Cl-pyridine-CH₃ | —CH₂C≡CH | —S-CH₂-cyclopropyl |
| 3-38 | 0 | Cl-pyridine-CH₃ | —CH₂C≡CH | —S-CH₂-cyclopentyl |

I-4

$$\text{Ar}-\text{CH}_2-\underset{R}{N}-(\text{CH}_2)_b-S-C(Y)=CH-CN$$

| Cmpd. No. | b | Ar | R | Y |
|---|---|---|---|---|
| 4-1 | 0 | Cl-pyridine-CH₃ | —CH₂C≡CH | N-(6-chloropyridin-3-ylmethyl)-N-(prop-2-ynyl)-2-(methylthio)ethylamine |
| 4-2 | 0 | Cl-pyridine-CH₃ | —CH₂CH₂OCH₃ | N-(6-chloropyridin-3-ylmethyl)-N-(2-methoxyethyl)-2-(methylthio)ethylamine |
| 4-3 | 0 | Cl-pyridine-CH₃ | —CH₂C≡N | N-(6-chloropyridin-3-ylmethyl)-N-(cyanomethyl)-2-(methylthio)ethylamine | where a is 1; b is 0 or 1, c is 0; R$^f$, R$^g$, R$^h$, R$^i$, R$^j$ and R$^k$ and are hydrogen, T is —S—, W is —N— and R$^7$ is —NO$_2$;
where a is 1; b is 0 or 1, c is 0; R$^f$, R$^g$, R$^h$, R$^i$, R$^j$ and R$^k$ and are hydrogen, T is —S—, W is —C— and R$^7$ is —NO$_2$;
where a is 1; b is 0 or 1, c is 0; R$^f$, R$^g$, R$^h$, R$^i$, R$^j$ and R$^k$ and are hydrogen, T is —S—, W is —N— and R$^7$ is —CN;
where a is 1; b is 0 or 1, c is 0; R$^f$, R$^g$, R$^h$, R$^i$, R$^j$ and R$^k$ and are hydrogen, T is —S—, W is —C— and R$^7$ is —CN;

The following table sets forth physical characterizing data for certain compounds of formula I of the present invention:

TABLE 2

Insecticidal (Heteroarylalkyl)alkane Thio and Oxo Amine Derivatives
Compound Characterization

| | Molecular Formula | Melting Point (° C.) of Solids Or Physical State |
|---|---|---|
| 1-1 | $C_{33}H_{36}Cl_2N_6O_4S_2$ | OIL |
| 1-2 | $C_{23}H_{24}Cl_2N_6O_2S_2$ | OIL |
| 1-3 | $C_{27}H_{40}Cl_2N_6O_2S_2$ | OIL |
| 1-4 | $C_{25}H_{36}Cl_2N_6O_2S_2$ | OIL |
| 1-5 | $C_{25}H_{32}Cl_2N_6O_2S_2$ | OIL |
| 1-6 | $C_{19}H_{20}Cl_2N_6O_2S_4$ | OIL |
| 1-7 | $C_{21}H_{32}Cl_2N_6O_2S_4$ | OIL |
| 1-8 | $C_{21}H_{22}Cl_2N_8O_2S_2$ | OIL |
| 1-9 | $C_{17}H_{18}Cl_2N_4O_2S_2$ | GUM |
| 1-10 | $C_{18}H_{21}ClN_4O_3S_2$ | OIL |
| 1-11 | $C_{11}H_{15}ClN_4O_2S_2$ | OIL |
| 1-12 | $C_{13}H_{15}ClN_4O_2S_2$ | OIL |
| 1-13 | $C_{15}H_{23}ClN_4O_2S_2$ | OIL |
| 1-14 | $C_{14}H_{21}ClN_4O_2S_2$ | OIL |
| 1-15 | $C_{14}H_{19}ClN_4O_2S_2$ | OIL |
| 1-16 | $C_{11}H_{13}ClN_4O_2S_3$ | OIL |
| 1-17 | $C_{12}H_{19}ClN_4O_2S_3$ | OIL |
| 1-18 | $C_{12}H_{14}ClN_5O_2S_2$ | OIL |
| 1-19 | $C_{14}H_{17}ClN_4O_2S_2$ | OIL |
| 1-20 | $C_{25}H_{28}Cl_2N_6O_2S_2$ | OIL |
| 1-21 | $C_{14}H_{21}ClN_4O_3S$ | OIL |
| 2-1 | $C_{32}H_{31}Cl_4N_5O_2S_2$ | OIL |
| 2-2 | $C_{24}H_{25}Cl_2N_5O_2S_2$ | OIL |
| 2-3 | $C_{34}H_{37}Cl_2N_5O_4S_2$ | OIL |
| 2-4 | $C_{26}H_{37}Cl_2N_5O_2S_2$ | OIL |
| 2-5 | $C_{28}H_{41}Cl_2N_5O_2S_2$ | OIL |
| 2-6 | $C_{26}H_{33}Cl_2N_5O_2S_2$ | OIL |
| 2-7 | $C_{20}H_{21}Cl_2N_5O_2S_4$ | OIL |
| 2-8 | $C_{22}H_{33}Cl_2N_5O_2S_4$ | OIL |
| 2-9 | $C_{22}H_{23}Cl_2N_7O_2S_2$ | OIL |
| 2-10 | $C_{24}H_{29}Cl_2N_5O_2S_2$ | OIL |
| 2-11 | $C_{12}H_{16}ClN_3O_2S_2$ | OIL |
| 2-12 | $C_{18}H_{19}Cl_2N_3O_2S_2$ | OIL |
| 2-13 | $C_{14}H_{16}ClN_3O_2S_2$ | OIL |
| 2-14 | $C_{19}H_{22}ClN_3O_3S_2$ | OIL |
| 2-15 | $C_{15}H_{22}ClN_3O_2S_2$ | OIL |
| 2-16 | $C_{16}H_{24}ClN_3O_2S_2$ | OIL |
| 2-17 | $C_{15}H_{20}ClN_3O_2S_2$ | OIL |
| 2-18 | $C_{12}H_{14}ClN_3O_2S_3$ | OIL |
| 2-19 | $C_{13}H_{20}ClN_3O_2S_3$ | OIL |
| 2-20 | $C_{13}H_{15}ClN_4O_2S_2$ | OIL |
| 2-21 | $C_{14}H_{18}ClN_3O_2S_2$ | OIL |
| 2-22 | $C_{15}H_{18}ClN_3O_2S_2$ | OIL |
| 2-23 | $C_{26}H_{29}Cl_2N_5O_2S_2$ | OIL |
| 2-24 | $C_{20}H_{26}ClN_3O_2S_2$ | OIL |
| 2-25 | $C_{14}H_{16}Cl_3N_3O_2S_2$ | OIL |
| 2-26 | $C_{24}H_{25}Cl_6N_5O_2S_2$ | OIL |
| 3-1 | $C_{30}H_{28}Cl_4N_8S_2$ | OIL |
| 3-2 | $C_{24}H_{24}Cl_2N_6S_2$ | OIL |
| 3-3 | $C_{26}H_{36}Cl_2N_6S_2$ | OIL |
| 3-4 | $C_{24}H_{32}Cl_2N_6S_2$ | OIL |
| 3-5 | $C_{36}H_{42}Cl_2N_8S_2$ | OIL |
| 3-6 | $C_{24}H_{32}Cl_2N_6O_2S_2$ | OIL |
| 3-7 | $C_{26}H_{32}Cl_2N_6S_2$ | OIL |
| 3-8 | $C_{21}H_{29}ClN_4S_2$ | OIL |
| 3-9 | $C_{20}H_{29}ClN_4OS_2$ | OIL |
| 3-10 | $C_{20}H_{25}ClN_4S_2$ | OIL |
| 3-11 | $C_{21}H_{31}ClN_4S_2$ | OIL |
| 3-12 | $C_{18}H_{27}ClN_4OS_2$ | OIL |
| 3-13 | $C_{19}H_{27}ClN_4S_2$ | OIL |
| 3-14 | $C_{19}H_{29}ClN_4S_2$ | OIL |
| 3-15 | $C_{22}H_{22}Cl_2N_8S_2$ | OIL |
| 3-16 | $C_{19}H_{17}ClN_4S_2$ | OIL |
| 3-17 | $C_{16}H_{15}ClN_4S_2$ | OIL |
| 3-18 | $C_{20}H_{19}ClN_4S_2$ | OIL |
| 3-19 | $C_{20}H_{20}Cl_2N_6S_4$ | OIL |
| 3-20 | $C_{24}H_{26}N_6S_2$ | OIL |
| 3-21 | $C_{14}H_{15}ClN_4S_2$ | SOLID |
| 3-22 | $C_{17}H_{17}ClF_2N_4S_2$ | OIL |
| 3-23 | $C_{22}H_{20}Cl_4N_8S_6$ | OIL |
| 3-24 | $C_{26}H_{28}Cl_2N_6S_2$ | OIL |
| 3-25 | $C_{14}H_{15}ClN_4S$ | OIL |
| 3-26 | $C_{15}H_{19}ClN_4S$ | OIL |
| 3-27 | $C_{22}H_{32}N_4O_2S_2$ | OIL |
| 3-28 | $C_{24}H_{24}Cl_6N_6S_2$ | OIL |
| 3-29 | $C_{19}H_{25}ClN_4S_2$ | OIL |
| 3-30 | $C_{21}H_{27}ClN_4S_2$ | OIL |
| 3-31 | $C_{20}H_{30}N_6O_2S_2$ | OIL |
| 3-32 | $C_{24}H_{28}Cl_2N_6S_2$ | OIL |
| 3-33 | $C_{24}H_{26}Cl_2N_8S_2$ | OIL |
| 3-34 | $C_{16}H_{15}ClN_4S_2$ | OIL |
| 3-35 | $C_{17}H_{21}ClN_4S_2$ | OIL |
| 3-36 | $C_{16}H_{19}ClN_4OS_2$ | OIL |
| 3-37 | $C_{17}H_{19}ClN_4S_2$ | OIL |
| 3-38 | $C_{19}H_{23}ClN_4S_2$ | OIL |
| 4-1 | $C_{25}H_{25}Cl_2N_5S_2$ | OIL |
| 4-2 | $C_{25}H_{33}Cl_2N_5O_2S_2$ | OIL |
| 4-3 | $C_{23}H_{23}Cl_2N_7S_2$ | OIL |

Candidate insecticides were evaluated for insecticidal activity by observing mortality in a population of cotton aphid (*Aphis gossypii*) on treated cotton plants when compared to like populations of cotton aphid on untreated plants. These tests were conducted in the following manner:

For each rate of application of test compound, two seven-to-ten days old cotton seedlings (*Gossypium hirsutium*) grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 1000 part per million (ppm) of each test compound was prepared by dissolving 10 milligrams of the test compound in 1 mL of acetone. Each solution was then diluted with 9 mL of a solution of 0.03 mL of polyoxyethylene(10) isooctylphenyl ether in 100 mL of water. About 2.5 mL of solution of each test compound was needed to spray each replicate of test plant (5 mL total for each test compound). If needed, the solution of 1000 ppm of test compound was serially diluted with a solution of 10% acetone and 300 ppm of polyoxyethylene (10) isooctylphenyl ether in water to provide solutions of each test compound for lower rates of application, for example, 300 ppm, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of 10% acetone and 300 ppm of polyoxyethylene (10) isooctylphenyl ether in water containing no test compound was also sprayed onto control test plants. Upon completion of spraying the solutions of test compound and the solution containing no test compound, the plants were allowed to dry. Upon completion of drying, the test and control plants were placed in a tray containing about 2.5 centimeters of water, where they were maintained in a growth chamber for 72 hours. After this time, each plant was assessed for percent mortality caused by the test compound when compared to the population of aphids that was infested onto the test plants prior to treatment with test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was less than 40% mortality of the cotton aphid, the test compound was termed as inactive (I).

An assessment of the insecticidal activity at selected rates of application from this test is provided in Tables 3 and 3A. The test compounds of formula I are identified by numbers that correspond to those in Table 1.

TABLE 3

The following Compounds of The Present Invention Reduced the Population of Cotton Aphid by At Least 75% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1-1 | 1-2 | 1-3 | 1-4 | 1-5 | 1-6 | 1-7 | 1-9 | 1-10 | 1-11 |
| 1-12 | 1-13 | 1-14 | 1-15 | 1-16 | 1-17 | 1-19 | 1-20 | 2-1 | 2-2 |
| 2-3 | 2-4 | 2-5 | 2-6 | 2-7 | 2-8 | 2-10 | 2-11 | 2-12 | 2-13 |
| 2-14 | 2-15 | 2-16 | 2-17 | 2-18 | 2-19 | 2-20 | 2-21 | 2-22 | 2-23 |
| 3-1 | 3-2 | 3-3 | 3-4 | 3-5 | 3-6 | 3-7 | 3-8 | 3-9 | 3-10 |
| 3-11 | 3-12 | 3-13 | 3-14 | 3-15 | 3-16 | 3-17 | 3-18 | 3-19 | 3-20 |
| 3-21 | 3-24 | 3-26 | | | | | | | |

TABLE 3A

The following Compounds of The Present Invention Reduced the Population of Cotton Aphid by 40% to 75% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 3-23 | 3-25 | | | | | | | | |

Candidate insecticides were also evaluated for cotton aphid insecticidal activity by observing mortality in a population of cotton aphid (*Aphis gossypii*) on treated cotton plant leaf discs when compared to like populations of cotton aphid on untreated plant leaf discs. These tests were conducted in the following manner:

Three week to one month-old cotton plants (*Gossypium hirsutium*) were prepared for infesting by cutting off the cotyledons and new true leaf growth, leaving the oldest two true leaves. To infest, two seven-to-ten day old cotton plants, grown in a cotton aphid colony were uprooted and lodged in the apex of the stem where the stems of the two true leaves meet with the main stem. Once infested, the test plants were maintained for up to about 12 hours to allow complete translocation of the aphids onto the leaves of the test plant. The wells of clear 128-well trays (CD-International, Pittman, N.J.) were filled with 1 mL of a warm, aqueous 3% agar solution and allowed to cool to ambient temperature. The aphid infested cotton leaves were removed from the plants and placed bottom side up on a cutting platform. Circular discs were cut from the infested leaves and placed bottom side up onto the cooled agar gel, one disc per well. Each leaf disc was visually inspected to assure that a minimum of 10 live aphids were present. A 50 mM stock solution of the test compound was prepared by dissolving the appropriate amount of the test compound in DMSO. A solution comprising 1000 part per million (ppm) of each test compound was prepared by dissolving 10 µl of the stock solution in 140 µl of an aqueous 0.003% Kinetic® (a nonionic wetter/spreader/penetrant adjuvant) solution. If needed, the solution of 1000 ppm of test compound was serially diluted with a solution of 66 mL of DMSO and 30 µl of Kinetic® in 934 mL of water (diluting solution) to provide solutions of each test compound for lower rates of application, for example, 300 ppm, 100 ppm, 30 ppm, or 10 ppm. Each replicate test plant disc was sprayed with 10 µl of the test solution at about 8 psi for 1 second. For comparison purposes, an aqueous solution of 0.003% Kinetic® containing no test compound and the diluting solution containing no test compound were also sprayed onto test plant discs. Upon completion of spraying the solutions of test compound and the solutions containing no test compound, the plant discs were allowed to dry. Upon completion of drying, the test trays were covered with a plastic film. Three slits were made in the film over each well to allow air into each well. The test trays were placed in a biochamber (25° C., 16 hours light, 8 hours of dark and 35-40% relative humidity) for three days. After this time, each plant disc was assessed for percent mortality caused by the test compound when compared to the population of aphids that was infested onto the test plant discs containing no test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was less than 40% mortality of the cotton aphid, the test compound was termed as inactive (I).

An assessment of the insecticidal activity at selected rates of application from this test is provided in Table 3B. The test compounds of formula I are identified by numbers that correspond to those in Table 1.

TABLE 3B

The Following Compounds of The Present Invention Reduced the Population of Cotton Aphid on Treated Leaf Disks by 40% to 100% When Applied at an Application Rate of 300 ppm or Less

| Cmpd. No. | Cmpd. No. | Cmpd. No. | Cmpd. No. | Cmpd. No. | Cmpd. No. | Cmpd. No. |
|---|---|---|---|---|---|---|
| 1-8 | 1-18 | 1-21 | 3-22 | 4-1 | 4-2 | 4-3 |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID#430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to thy, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.25, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed for insecticidal activity. A test compound was designated as possessing insecticidal activity (SA) if there was 40% to 75% mortality of tobacco budworm on diet treated with that compound. If there was 75% mortality or greater of the tobacco budworm, a test compound was designated as being more insecticidally active (A). If there was less than 40% mortality of the tobacco budworm, the test compound was termed as inactive (I).

Insecticidal activity data at selected rates of application from this test are provided in Table 4. The test compounds of formula I are identified by numbers that correspond to those in Table 1.

Concentration of the candidate insecticide on the surface of the diet is 0.25 millimolar.

Candidate insecticides were evaluated for insecticidal activity by observing mortality in a population of silverleaf whitefly (*Bemisia argentifolii*) on treated cotton plant cotyledons when compared to like populations of silverleaf whitefly on untreated plant cotyledons. These tests were conducted in the following manner:

For each rate of application of test compound, two four to six days old cotton seedlings (*Gossypium hirsutium*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (5 mL total for each test compound). If needed, the solution of 300 ppm of test compound was diluted with a solution of 10% acetone and 300 ppm of Triton X-100® surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the test plants were excised at the soil surface and placed in a 1 ounce plastic cup containing a 2.5 cm filter paper moistened with 50 microliters of distilled water. Whiteflies (25-50) were added to each cup and a lid was placed on each. The test cups were maintained in a growth chamber for 72 hours at 70% relative humidity (light 12 hours/day). After this time, each test was assessed for percent mortality caused by the test compound when compared to the population of whiteflies that were infested onto the test plants. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was less than 40% mortality of the cotton aphid, the test compound was termed as inactive (I).

An assessment of the insecticidal activity at selected rates of application from this test is provided in Table 5. The test compounds of formula I are identified by numbers that correspond to those in Table 1.

TABLE 4

The Following Compounds of The Present Invention Reduced the Population of Tobacco Budworm (*Heliothis virescens* [Fabricius]) When Applied to the Surface of the Diet by 75% or more

| Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|
| 1-6 | 1-16 | 2-1 | 2-2 | 2-4 | 2-5 | 2-6 | 2-7 | 2-8 |
| 2-9 | 2-10 | 2-11 | 2-12 | 2-13 | 2-14 | 2-15 | 2-16 | 2-17 |
| 2-18 | 2-20 | 2-21 | 2-22 | 2-23 | 3-1 | 3-2 | 3-4 | 3-6 |
| 3-7 | 3-8 | 3-10 | 3-11 | 3-12 | 3-13 | 3-14 | 3-15 | 3-16 |
| 3-17 | 3-19 | 3-21 | 3-24 | 4-1 | | | | |

TABLE 5

The Following Compounds of The Present Invention Reduced the Population of Silverleaf Whitefly (*Bemisia argentifolii*) by at Least 40% When Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1-5 | 1-15 | 1-17 | 2-2 | 2-4 | 2-5 | 2-6 | 2-7 | 2-8 | 2-10 |
| 2-15 | 2-16 | 2-17 | 2-18 | 2-20 | 2-21 | 2-22 | 2-23 | 3-1 | 3-3 |
| 3-4 | 3-5 | 3-6 | 3-7 | 3-8 | 3-10 | 3-11 | 3-13 | 3-14 | 3-18 |
| 3-21 | 3-25 | | | | | | | | |

Candidate insecticides were evaluated for insecticidal activity by observing mortality in a population of Western Tarnished Plant Bug nymphs (*Lygus hesperus*) on treated broccoli plant leaves when compared to like populations of tarnished plant bug on untreated plant leaves. These tests were conducted in the following manner:

For each rate of application of test compound, four ten to fifteen days old broccoli seedlings (*Brassica oleracea*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (10 mL total for each test compound). If needed, the solution of 300 ppm of test compound was diluted with a solution of 10% acetone and 300 ppm of Triton X-100® surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the treated foliage was removed and two leaves were placed into an 8 ounce unwaxed paper cup which contained a one inch piece of cut cotton wick, moistened by soaking for five seconds with distilled water. Four late second to early third instar tarnished plant bug nymphs were placed into each cup and a lid was placed on each. The test cups were maintained in a growth chamber for 72 hours at 70% relative humidity (light 12 hours/day). After this time, each test was assessed for percent mortality caused by the test compound when compared to the population of tarnished plant bug nymphs that were infested onto the test plant leaves. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was less than 40% mortality of the cotton aphid, the test compound was termed as inactive (I).

An assessment of the insecticidal activity at selected rates of application from this test is provided in Table 6. The test compounds of formula I are identified by numbers that correspond to those in Table 1.

TABLE 6

The Following Compounds of The Present Invention Reduced the Population of Westeren Tarnished Plant Bug Nymphs (Lygus hesperus) by at Least 40% When Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 2-2 | 2-4 | 2-5 | 2-6 | 2-10 | 2-15 | 2-16 | 2-17 | 2-18 | 2-21 |
| 2-22 | 2-23 | 3-2 | 3-21 | 3-23 | | | | | |

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I

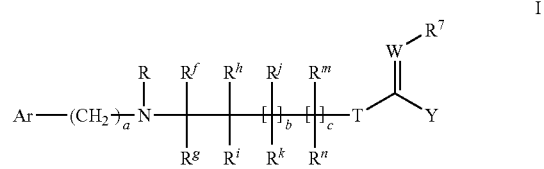

where

Ar is selected from

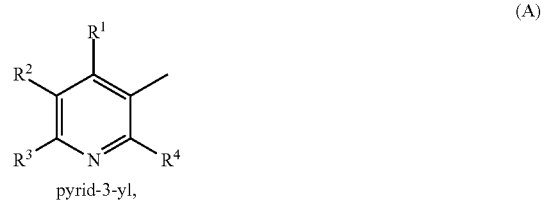

pyrid-3-yl,

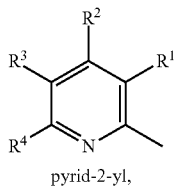
pyrid-2-yl, (A1)

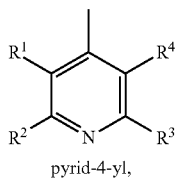
pyrid-4-yl, (A2)

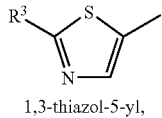
1,3-thiazol-5-yl, (B)

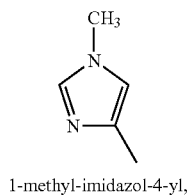
1-methyl-imidazol-4-yl, (C)

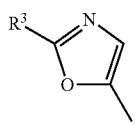
1,3-oxazol-5-yl, (D)

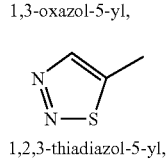
1,2,3-thiadiazol-5-yl, (E)

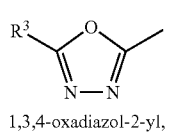
1,3,4-oxadiazol-2-yl, (F)

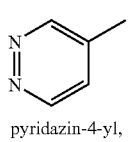
pyridazin-4-yl, (G)

where
$R^1$, $R^2$, $R^3$, and $R^4$ are independently selected from hydrogen, halogen, alkyl, alkoxy, haloalkyl, and haloalkoxy;
and,
a is an integer selected from 0 or 1;
R is selected from hydroxy, alkyl, haloalkyl, alkoxyalkyl, alkoxyalkoxyalkyl, cyanoalkyl, formyl, alkylcarbonyl, alkoxycarbonyl, alkylsulfonyl, dialkylphosphonato,

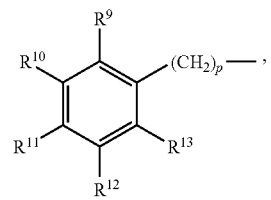
(1)

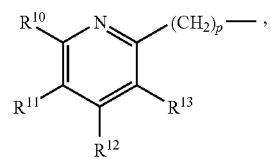
(2)

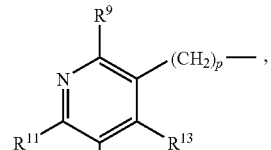
(3)

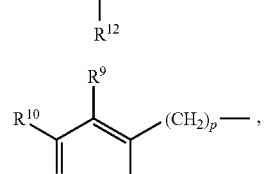
(4)

—$(CH_2)_p$—$CR^{14}$=$CR^{15}R^{16}$  and (5)

—$(CH_2)_p$—C≡$CR^{17}$, (6)

where
p is an integer selected from 1 or 2;
and,
$R^9$, $R^{10}$, $R^{11}$, $R^{12}$, and $R^{13}$ are independently selected from hydrogen, halogen, alkyl, haloalkyl, alkoxy, haloalkoxy, alkoxyimino, dialkylaminoalkyl, cyano, nitro, 2-alkyl-2H-tetrazol-5-yl, aryl, and aryloxy;
$R^{14}$, $R^{15}$ and $R^{16}$ are independently selected from hydrogen, halogen, and alkyl;
$R^{17}$ is selected from hydrogen, alkyl, and

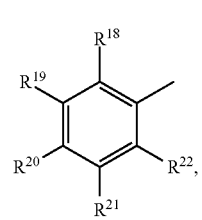
(7)

where
$R^{18}$, $R^{19}$, $R^{20}$, $R^{21}$, and $R^{22}$ are independently selected from hydrogen, halogen, alkyl, haloalkyl, alkoxy, and haloalkoxy;
b and c are integers independently selected from 0 or 1;
$R^f$, $R^g$, $R^h$, $R^i$, $R^j$, $R^k$, $R^m$ and $R^n$ are independently selected from hydrogen and alkyl;
T is selected from —O—, —S—, —$CR^{34}R^{35}$—;

Y is selected from —X—$R^6$ and

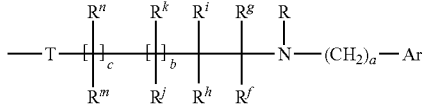
(9)

where

X is selected from —O—, —S—, and —$CR^{34}R^{35}$—;

$R^6$ is selected from hydrogen, alkyl, cycloalkyl, cycloalkylalkyl, alkoxy, alkoxyalkyl, alkoxyalkoxyalkyl, alkenyl, haloalkenyl, alkynyl and

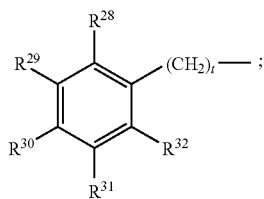
(10)

where t is an integer selected from 0, 1 and 2;

and, $R^{28}$, $R^{29}$, $R^{30}$, $R^{31}$ and $R^{32}$ are independently selected from hydrogen, halogen, alkyl, haloalkyl, alkoxy, and haloalkoxy;

Ar, R, $R^f$, $R^g$, $R^h$, $R^i$, $R^j$, $R^k$, $R^m$, $R^n$, a, b and c have the same meaning as stated above;

$R^7$ is selected from —C≡N and —$NO_2$;

W is selected from —$CR^{33}$— and —N—;

$R^{33}$, $R^{34}$, and $R^{35}$ are independently selected from hydrogen and alkyl;

where provided that when i) Ar is pyrid-3-yl (A); ii) a is 1 and b and c are 0 and $R^f$ through $R^i$, inclusively, are hydrogen; iii) R is cycloalkylalkyl; iv) T is —S—; v) $R^7$ is —C≡N; and v) Y is

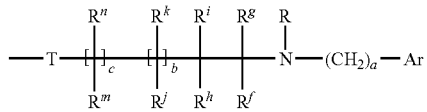

where Ar, R, $R^f$, $R^g$, $R^h$, $R^i$, a, b and c have the same meaning as stated above; vi) then W is —N—;

the N-oxides thereof; and agriculturally acceptable salts thereof.

2. A compound of claim 1, wherein a is 1; b and c are each 0; $R^f$, $R^g$, $R^h$ and $R^i$ are each hydrogen; W is selected from —$CR^{33}$— and —N—, where $R^{33}$ is hydrogen; and T and X are each —S—.

3. A compound of claim 2, wherein Ar is

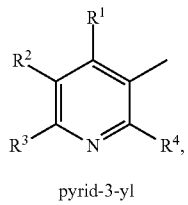
(A)

pyrid-3-yl where $R^1$, $R^2$ and $R^4$ are each hydrogen and $R^3$ is halogen.

4. A composition comprising an insecticidally effective amount of a compound of claim 1 and at least one agriculturally acceptable extender or adjuvant.

5. The insecticidal composition of claim 4, further comprising one or more additional compounds selected from the group consisting of pesticides, plant growth regulators, fertilizers and soil conditioners.

6. A method of controlling insects, comprising applying an insecticidally effective amount of a composition of claim 4 to a locus where insects are present or are expected to be present.

7. A method of controlling insects, comprising applying an insecticidally effective amount of a composition of claim 5 to a locus where insects are present or are expected to be present.

* * * * *

UNITED STATES PATENT AND TRADEMARK OFFICE
CERTIFICATE OF CORRECTION

PATENT NO. : 7,932,393 B2  
APPLICATION NO. : 12/223279  
DATED : April 26, 2011  
INVENTOR(S) : John F. Chiarello Page 1 of 1

It is certified that error appears in the above-identified patent and that said Letters Patent is hereby corrected as shown below:

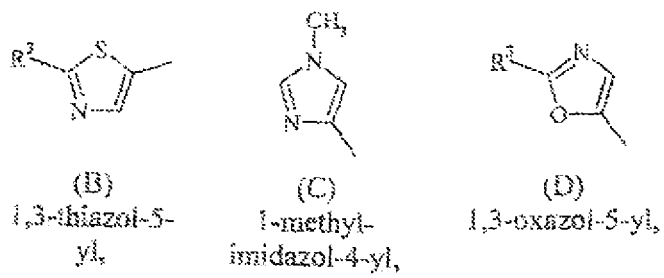

Column 55, lines 18-55, delete "

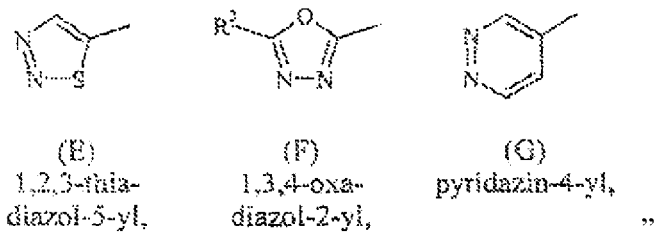

"

Signed and Sealed this  
Twenty-first Day of June, 2011

David J. Kappos  
*Director of the United States Patent and Trademark Office*